United States Patent
Orme et al.

(10) Patent No.: US 7,022,856 B2
(45) Date of Patent: *Apr. 4, 2006

(54) CARBOLINE DERIVATIVES

(75) Inventors: Mark W. Orme, Seattle, WA (US); Jason S. Sawyer, Indianapolis, IN (US); Agnes Bombrun, Monnetier (FR); Romain L. Gosmini, Les Ulis (FR); Anne Bouillot, Les Ulis (FR); Nerina Dodic, Les Ulis (FR); Michael Sierra, Les Ulis (FR)

(73) Assignee: LIlly Icos LLC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/470,407

(22) PCT Filed: Dec. 18, 2001

(86) PCT No.: PCT/US01/49393

§ 371 (c)(1),
(2), (4) Date: Feb. 12, 2004

(87) PCT Pub. No.: WO02/064590

PCT Pub. Date: Aug. 22, 2002

(65) Prior Publication Data

US 2004/0122035 A1    Jun. 24, 2004

Related U.S. Application Data

(60) Provisional application No. 60/268,158, filed on Feb. 12, 2001.

(51) Int. Cl.
*C07D 471/04* (2006.01)
*A61K 31/437* (2006.01)

(52) U.S. Cl. .............. 546/85; 546/86; 546/87; 544/277; 544/284; 544/331; 544/333; 544/122; 514/235.8; 514/256; 514/263.22; 514/266.21; 514/275; 514/292

(58) Field of Classification Search ........... 546/85, 546/86, 87; 544/277, 284, 331, 333, 122; 514/292, 256, 266.21, 275, 263.22, 235.8
See application file for complete search history.

(56) References Cited

U.S. PATENT DOCUMENTS 6,492,358 B1 * 12/2002 Sui et al. ............... 514/232.8

FOREIGN PATENT DOCUMENTS

| JP | 3287586 | 12/1991 |
|----|---------|---------|
| WO | WO 97/43287 | 11/1997 |
| WO | WO 00/72846 | * 12/2000 |
| WO | WO 01/87038 | 11/2001 |
| WO | WO 01/87882 | 11/2001 |
| WO | WO 02/062339 | 8/2002 |

OTHER PUBLICATIONS

Ukita et al. J. Med. Chem. 2001. 44:2204-2218.*
Rotella D. Nature Reviews/Drug Discovery. 2002. 1:674-682.*
C. Gremmen et al., *Organic Letters*, 2(13), 1955-1958 (2000).
Y. You et al., *Hecheng Huaxue Bianjibu*, 8(1), 83-86 (2000).
T. Kawate et al., *Heterocycles*, 50(2), 1033-1039 (1999).
J. Carniaux et al., *Tetrahedron Letters*, 38(17), 2997-3000 (1997).
B. Legseir et al., *Journal de la Societe Algerienne de Chimie*, 6(1), 17-27 (1996).
T. Soe et al., *Tetrahedron Letters*, 36(11), 1857-60 (1995).
R.L. Parsons et al., *Journal of Organic Chemistry*, 58(26), 7482-9 (1993).
D. Soerens et al., *J. Org. Chem.*, 44(4), 535-45 (1979).
T.H. Yang et al., *Chung-Hua Yao Hsueh Tsa Chih*, 41(3), 239-46 (1989).
S. Misztal, *Diss. Pharm. Pharmacol.*, 23(4), 409-17 (1971).
A.H. Jackson et al., *Tetrahedron*, 24(1), 403-13 (1968).

(Continued)

*Primary Examiner*—Bernard Dentz
(74) *Attorney, Agent, or Firm*—Marshall, Gerstein & Borun LLP

(57) ABSTRACT

Compounds of the general structural formula

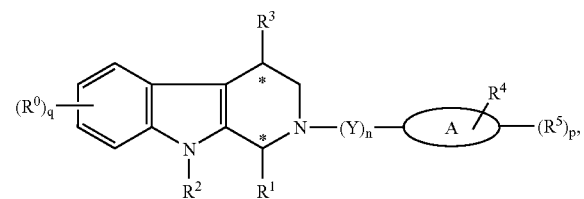

and use of the compounds and salts and solvates thereof, as therapeutic agents.

18 Claims, No Drawings

OTHER PUBLICATIONS

M.A. Seefeld et al., *Bioorganic & Medicinal Chemistry Letters*, 11(17), 2241-2244 (2001).

S. Chernov et al., *Doklady Akademii Nauk.*, 381(5), 643-646 (2001).

* cited by examiner

CARBOLINE DERIVATIVES

CROSS-REFERENCE TO RELATED APPLICATIONS

This is the U.S. national phase application of International Application No. PCT/US01/49393, filed Dec. 18, 2001, which claims the benefit of U.S. provisional patent application Ser. No. 60/268,158, filed Feb. 12, 2001.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

SUMMARY OF THE INVENTION

The present invention provides compounds of formula (I)

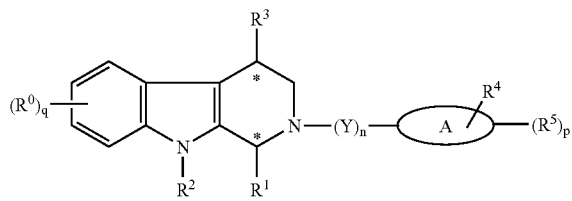

(I)

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, $C(=O)R^a$, $OC(=O)R^a$, $C(=O)OR^a$, $C_{1-4}$alkyleneNR$^a$R$^b$, $C_{1-4}$alkyleneHet, $C_{1-4}$alkyleneC(=O)OR$^a$, $C(=O)NR^a SO_2R^c$, $C(=O)C_{1-4}$alkyleneHet, $C(=O)NR^a R^b$, $C(=O)NR^b R^c$, $C(=O)NR^a C_{1-4}$alkyleneOR$^b$, $C(=O)NR^a C_{1-4}$alkyleneHet, $OR^a$, $OC_{1-4}$alkyleneC(=O)OR$^a$, $OC_{1-4}$alkyleneNR$^a$R$^b$, $OC_{1-4}$alkyleneHet, $OC_{1-4}$alkyleneOR$^a$, $OC_{1-4}$alkyleneNR$^a$C(=O)OR$^b$, $NR^a R^b$, $NR^b R^c$, $NR^a C_{1-4}$alkyleneNR$^a$R$^b$, $NR^a C(=O)R^b$, $NR^a C(=O)NR^a R^b$, $N(SO_2C_{1-4}$alkyl$)_2$, $NR^a(SO_2C_{1-4}$alkyl), nitro, trifluoromethyl, trifluoromethoxy, cyano, $SO_2NR^a R^b$, $SO_2R^a$, $SOR^a$, $SR^a$, and $OSO_2CF_3$;

$R^1$ is selected from the group consisting of optionally substituted aryl, optionally substituted heteroaryl, an optionally substituted $C_{3-8}$cycloalkyl ring, an optionally substituted $C_{3-8}$heterocycloalkyl ring, an optionally substituted bicyclic ring

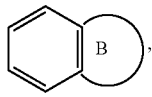

wherein the fused ring B is a 5- or 6-membered ring, saturated or partially or fully unsaturated, and comprises carbon atoms and optionally one to three heteroatoms selected from oxygen, sulfur, and nitrogen, hydrogen, $C_{1-6}$alkyl, arylC$_{1-3}$alkyl, $C_{1-3}$alkenylenearyl, haloC$_{1-6}$alkyl, $C_{1-4}$alkyleneC(=O)OR$^a$, $C_{1-4}$alkyleneC(=O)NR$^a$R$^b$, $C_{3-8}$cycloalkyl, $C_{3-8}$cycloalkenyl, $C_{3-8}$heterocycloalkenyl, $C_{1-4}$alkyleneHet, $C_{1-4}$alkyleneQR$^a$, $C_{2-6}$alkenyleneQR$^a$, $C_{1-4}$alkyleneQC$_{1-4}$alkyleneQR$^a$,

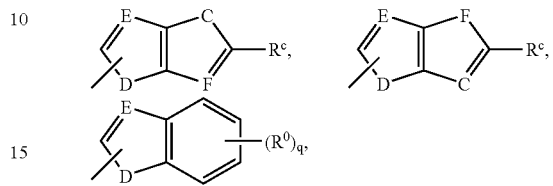

and a spiro substituent having a structure

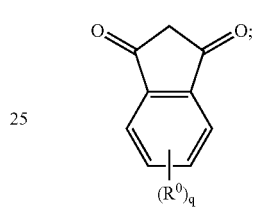

$R^2$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, arylC$_{1-3}$alkyl, aryl, heteroaryl, $C(=O)R^a$, $C(=O)NR^a R^b$, $C(=O)NR^b R^c$, $C(=S)NR^a R^b$, $C(=S)NR^b R^c$, $OR^a$, $NR^a R^b$, $NR^b R^c$, $SO_2R^a$, $SO_2NR^a R^b$, $S(=O)R^a$, $S(=O)NR^a R^b$, $C(=O)NR^a C_{1-4}$alkyleneOR$^a$, $C(=O)NR^a C_{1-4}$alkyleneHet, $C(=O)C_{1-4}$alkylenearyl, $C(=O)C_{1-4}$alkyleneheteroaryl, $C_{1-4}$alkylenearyl, $C_{1-4}$alkyleneheteroaryl, $C_{1-4}$alkyleneHet, $C_{1-4}$alkyleneC(=O)C$_{1-4}$alkylenearyl, $C_{1-4}$alkyleneC(=O)C$_{1-4}$alkyleneheteroaryl, $C_{1-4}$alkyleneC(=O)Het, $C_{1-4}$alkyleneC(=O)NR$^b$R$^c$, $C_{1-4}$alkyleneOR$^a$, $C_{1-4}$alkyleneNR$^a$C(=O)R$^a$, $C_{1-4}$alkyleneOC$_{1-4}$alkyleneOR$^a$, $C_{1-4}$alkyleneNR$^b$R$^c$, $C_{1-4}$alkyleneC(=O)OR$^a$, and $C_{1-4}$alkyleneOC$_{1-4}$alkyleneC(=O)OR$^a$;

$R^3$ is selected from the group consisting of hydrogen, $C_{1-6}$alkyl, haloC$_{1-6}$alkyl, aryl, heteroaryl, arylC$_{1-3}$alkyl, heteroarylC$_{1-3}$alkyl, $C_{1-3}$alkylenearyl, $C_{1-3}$alkyleneHet, $C_{3-8}$cycloalkyl, and $C_{3-8}$heterocycloalkyl;

Y is selected from the group consisting of $C(=O)$, $C(=O)Z$, $SO$, $SO_2$, $C(=S)$, $C(R^a)_2$, and $CR^a=CR^a$;

Z is $(CH_2)_t$ or $C\equiv C$;

A is aryl or heteroaryl and is selected from the group consisting of optionally substituted 5- or 6-membered aromatic rings and optionally substituted fused bicyclic ring systems, either carbocyclic or containing at least one heteroatom selected from the group consisting of oxygen, nitrogen, and sulfur, and containing at least one aromatic ring;

$R^4$ is selected from the group consisting of hydrogen, $C_{1-6}$alkyl, aryl, heteroaryl, halo, $C(=O)OR^b$, $NHC(=O)$ $C_{1-3}$ alkyleneN(R$^b$)$_2$, $NO_2$, $C(=O)OR^b$, $OR^b$, $CF_3$, $OR^a$, $CN$, $OC(=O)R^b$, arylOR$^b$, Het, $NR^a C(=O)C_{1-3}$alkyleneC(=O)OR$^a$, arylOC$_{1-3}$alkyleneNR$^a$R$^b$, arylOC(=O)R$^a$, $C_{1-4}$alkyleneC(=O)OR$^b$, $OC_{1-4}$alkyleneC(=O)OR$^b$, $C_{1-4}$alkyleneOC$_{1-4}$alkyleneC(=O)OR$^b$, $C(=O)NR^b SO_2R^c$, $C_{1-4}$alkyleneNR$^b$R$^c$, $C_{2-6}$alkenyleneNR$^b$R$^c$, $C(=O)$ $NR^b C_{1-4}$ alkyleneOR$^b$, $C(=O)NR^b C_{1-4}$alkyleneHet, $OC_{2-4}$ alkyleneNR$^b$R$^c$, OC$_{1-4}$alkyleneCH(OR$^b$)CH$_2$NR$^b$R$^c$, OC$_{1-4}$alkyleneHet, OC$_{2-4}$alkyleneOR$^b$, OC$_{2-4}$alkyleneNR$^b$C(=O)OR$^c$, NR$^b$C$_{1-4}$alkyleneNR$^b$R$^c$, NR$^b$C(=O)R$^c$, NR$^b$C(=O)NR$^b$R$^c$, N(SO$_2$C$_{1-4}$alkyl)$_2$, NR$^b$(SO$_2$C$_{1-4}$alkyl), SO$_2$NR$^b$R$^c$, OSO$_2$CF$_3$, C(=O)R$^b$, C$_{1-3}$alkylenearyl, C$_{1-4}$alkyleneHet, C$_{1-6}$alkyleneOR$^b$, C$_{1-3}$alkyleneN(R$^b$)$_2$, NR$^b$R$^c$, C(=O)NR$^b$R$^c$, NHC(=O)C$_{1-3}$alkylenearyl, NHC(=O)C$_{1-3}$alkyleneheteroaryl, C$_{3-8}$cycloalkyl, C$_{3-8}$heterocycloalkyl, arylOC$_{1-3}$alkyleneN(R$^b$)$_2$, arylOC(=O)R$^b$, NHC(=O)C$_{1-3}$alkyleneC$_{3-8}$heterocycloalkyl, NHC(=O)C$_{1-3}$alkyleneHet, NHC(=O)haloC$_{1-6}$alkyl, and

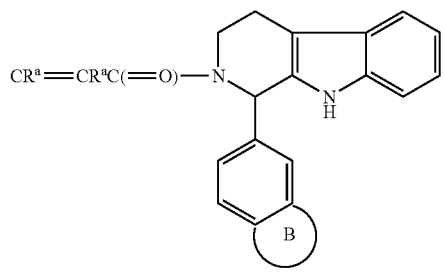

R$^5$, independently, is selected from the group consisting of halo, NR$^a$R$^b$, NO$_2$, C$_{1-6}$alkyl, oxo, and OR$^a$;

or R$^4$ and R$^5$ are taken together to form a 3- or 4-membered alkylene or alkenylene chain component of a 5- or 6-membered ring, optionally containing at least one heteroatom;

R$^a$ is selected from the group consisting of hydrogen, C$_{1-6}$alkyl, cyano, aryl, arylC$_{1-3}$alkyl, C$_{1-3}$alkylenearyl, heteroaryl, heteroarylC$_{1-3}$alkyl, and C$_{1-3}$alkyleneheteroaryl;

R$^b$ is selected from the group consisting of hydrogen, C$_{1-6}$alkyl, C$_{3-8}$cycloalkyl, C$_{1-3}$alkyleneN(R$^a$)$_2$, aryl, arylC$_{1-3}$alkyl, C$_{1-3}$alkylenearyl, heteroaryl, heteroarylC$_{1-3}$alkyl, and C$_{1-3}$alkyleneheteroaryl;

R$^c$ is selected from the group consisting of hydrogen, C$_{1-6}$alkyl, aryl, heteroaryl, arylC$_{1-3}$alkyl, heteroarylC$_{1-3}$alkyl, C$_{1-3}$alkyleneN(R$^a$)$_2$, C$_{1-6}$alkylenearyl, C$_{1-6}$alkyleneHet, haloC$_{1-6}$alkyl, C$_{3-8}$cycloalkyl, C$_{3-8}$heterocycloalkyl, Het, C$_{1-3}$alkyleneheteroaryl, C$_{1-6}$alkyleneC(=O)OR$^a$, and C$_{1-3}$alkyleneC$_{3-8}$heterocycloalkyl;

or R$^b$ and R$^c$ are taken together to form a 5- or 6-membered ring, optionally containing at least one heteroatom;

Q is O, S, or NR$^d$;
C is O, S, or NR$^d$;
D is O, S, or NR$^d$;
E is CR$^a$ or N;
F is CR$^a$, C(R$^a$)$_2$, or NR$^d$;

R$^d$ is null or is selected from the group consisting of hydrogen, C$_{1-6}$alkyl, aryl, heteroaryl, arylC$_{1-3}$alkyl, heteroarylC$_{1-3}$alkyl, C$_{1-3}$alkylenearyl, and C$_{1-3}$alkyleneheteroaryl;

Het is a 5- or 6-membered heterocyclic ring, saturated or partially or fully unsaturated, containing at least one heteroatom selected from the group consisting of oxygen, nitrogen, and sulfur, and optionally substituted with C$_{1-4}$alkyl or C(=O)OR$^a$;

n is 0 or 1;
p is 0, 1, 2, or 3;
q is 0, 1, 2, 3, or 4;
t is 1, 2, 3, or 4;

and pharmaceutically acceptable salts and solvates (e.g., hydrates) thereof.

In a preferred embodiment, R$^2$ and R$^3$ is hydrogen, q is 0, and the compounds have a structural formula (II):

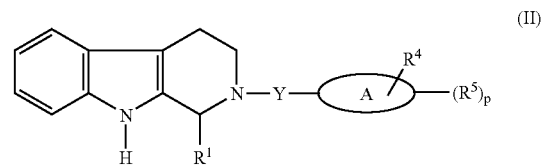

(II)

wherein R$^1$ is selected from the group consisting of optionally substituted aryl, optionally substituted heteroaryl, an optionally substituted bicyclic ring

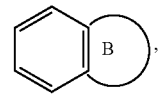

wherein the fused ring B is a 5- or 6-membered ring, saturated or partially or fully unsaturated, and comprises carbon atoms and optionally one to three heteroatoms selected from oxygen, sulfur, and nitrogen;

Y null or is selected from the group consisting of C(=O), C(=O)C≡C, C(=O)(CH$_2$)$_t$, SO$_2$, and C(=S);

A is aryl or heteroaryl and is selected from the group consisting of optionally substituted 5- or 6-membered aromatic rings and optionally substituted fused bicyclic ring systems, either carbocyclic or containing at least one heteroatom selected from the group consisting of oxygen, nitrogen, and sulfur, and containing at least one aromatic ring;

R$^4$ is selected from the group consisting of hydrogen, C$_{1-6}$alkyl, aryl, heteroaryl, halo, C(=O)OR$^b$, NHC(=O)C$_{1-3}$ alkyleneN(R$^b$)$_2$, NO$_2$, C(=O)OR$^b$, OR$^b$, CF$_3$, OR$^a$, CN, OC(=O)R$^b$, arylOR$^b$, Het, NR$^a$C(=O)C$_{1-3}$alkyleneC(=O)OR$^a$, arylOC$_{1-3}$alkyleneNR$^a$R$^b$, arylOC(=O)R$^a$, C$_{1-4}$alkyleneC(=O)OR$^b$, OC$_{1-4}$alkyleneC(=O)OR$^b$, C(=O)NR$^b$SO$_2$R$^c$, C$_{1-4}$alkyleneNR$^b$R$^c$, C$_{2-6}$alkyleneNR$^b$R$^c$, C(=O)NR$^b$C$_{1-4}$alkyleneOR$^b$, NR$^b$C$_{1-4}$alkyleneNR$^b$R$^c$, NR$^b$C(=O)R$^c$, NR$^b$C(=O)NR$^b$R$^c$, OSO$_2$CF$_3$, C(=O)R$^b$, C$_{1-3}$alkylenearyl, C$_{1-4}$alkyleneHet, C$_{1-6}$alkyleneOR$^b$, C$_{1-3}$alkyleneN(R$^b$)$_2$, NR$^b$R$^c$, C(=O)NR$^b$R$^c$, NHC(=O)C$_1$–C$_3$alkylenearyl, NHC(=O)C$_{1-3}$alkyleneheteroaryl, NHC(=O)C$_{1-3}$alkyleneC$_{3-8}$heterocycloalkyl, NHC(=O)C$_{1-3}$alkyleneHet, NHC(=O)haloC$_{1-6}$alkyl, and

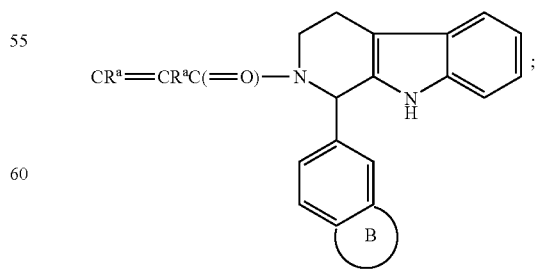

R$^5$, independently, is selected from the group consisting of halo, NR$^a$R$^b$, NO$_2$, C$_{1-6}$alkyl, oxo, and OR$^a$;

$R^a$ and $R^b$, independently, are selected from the group consisting of hydrogen, $C_{1-6}$alkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^c$ is selected from the group consisting of hydrogen, $C_{1-6}$alkyl, aryl, heteroaryl, aryl$C_{1-3}$alkyl, heteroaryl$C_{1-3}$alkyl, $C_{1-3}$alkyleneN$(R^a)_2$, $C_{1-6}$alkylenearyl, $C_{1-6}$alkyleneHet, halo$C_{1-6}$alkyl, $C_{3-8}$cycloalkyl, $C_{3-8}$heterocycloalkyl, Het, $C_{1-3}$alkyleneheteroaryl, $C_{1-6}$alkyleneC(=O)OR$^a$, and $C_{1-3}$alkyleneC$_{3-8}$heterocycloalkyl;

or $R^b$ and $R^c$ are taken together to form a 5- or 6-membered ring, optionally containing at least one heteroatom;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^a$;

p is 0, 1, 2, or 3;

t is 1, 2, 3, or 4;

and pharmaceutically acceptable salts and solvates (e.g., hydrates) thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl. "Heterocycloalkyl" is defined similarly as cycloalkyl except the ring contains one to three heteroatoms selected from the group consisting of oxygen, nitrogen, and sulfur.

The term "alkenyl" is defined identically as "alkyl," except for containing a carbon-carbon double bond. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl", is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, NHC(=O)$C_{1-3}$alkyl, OC$_{1-3}$alkyleneNR$^a$R$^b$, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl", are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as a 5- or 6-membered heterocycle containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxy" is defined as —OCF$_3$.

The term "spiro" as used herein refers to a group having two carbon atoms directly bonded to the carbon atom to which $R^1$ is attached.

The term "cyano" is defined as —CN.

In a preferred embodiment, q is 0. In other preferred embodiments, $R^0$ is selected from the group consisting of $C_{1-6}$alkyl, aryl, heteroaryl, Het, OR$^a$, C(=O)OR$^a$, $C_{1-4}$alkyleneNR$^a$R$^b$, OC(=O)R$^a$, C(=O)R$^a$, NR$^a$R$^b$, $C_{3-8}$cycloalkyl, $C_{3-8}$cycloalkylQ, C(=O)NR$^a$R$^b$, and C(=O)NR$^b$R$^c$.

In a preferred group of compounds of formula (I), $R^1$ is represented by

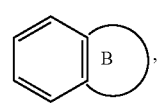

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

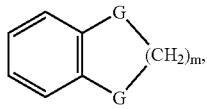

wherein m is an integer 1 or 2, and G, independently, is $C(R^a)_2$, O, S, or $NR^a$. The bicyclic ring comprising the $R^1$ substituent typically is attached to the rest of the molecule by a phenyl ring carbon atom.

In a more preferred group of compounds of formula (I), $R^1$ is represented by an optionally substituted bicyclic ring

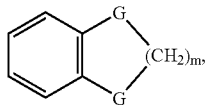

wherein m is 1 or 2, and G, independently, are $C(R^a)_2$ or O. Especially preferred $R^1$ substituents include

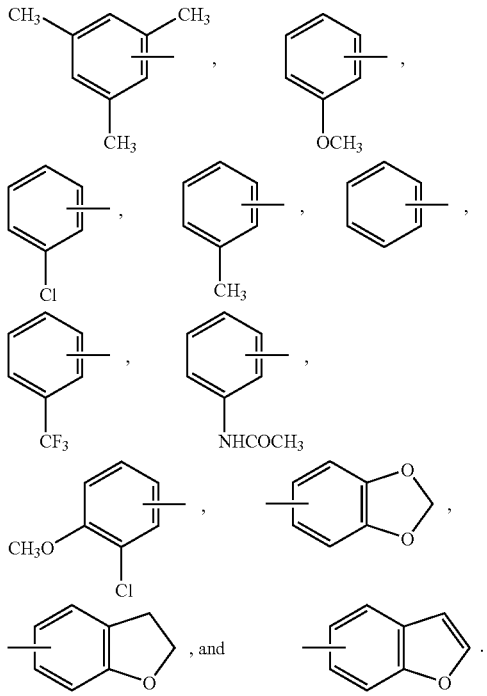

Within this particular group of compounds, nonlimiting examples of substituents for the aromatic ring include halogen (e.g., chlorine), $C_{1-3}$alkyl (e.g., methyl, ethyl, or i-propyl), $OR^a$ (e.g., methoxy, ethoxy, or hydroxy), $CO_2R^a$, halomethyl or halomethoxy (e.g., trifluoromethyl or trifluoromethoxy), cyano, $NR^aC(=O)R^a$, nitro, and $NR^aR^b$.

In other preferred embodiments, $R^1$ is optionally substituted and selected from the group consisting of $C_{1-4}$alkyleneQ$R^a$, $C_{1-4}$alkyleneQ$C_{1-4}$alkyleneQ$R^a$, $C_{3-8}$cycloalkyl, $C_{3-8}$cycloalkenyl, $C_{1-6}$alkyl,

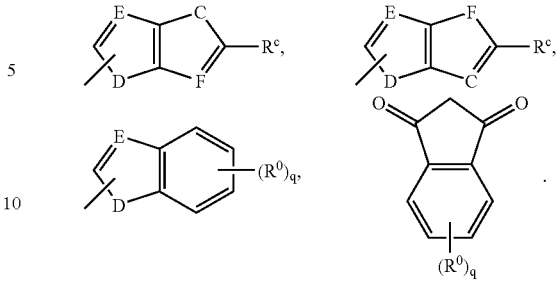

In a more preferred group of compounds of formula (I), $R^1$ is represented by

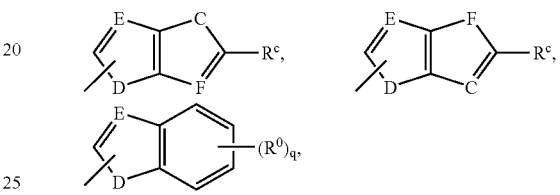

$C_{3-8}$cycloalkyl, $C_{3-8}$cycloalkenyl, $C_{1-6}$alkyl, $C_{1-4}$alkyleneQ$R^a$, and $C_{1-4}$alkyleneQ$C_{1-4}$alkyleneQ$R^a$. A preferred Q is oxygen.

Some preferred $R^1$ substituents are

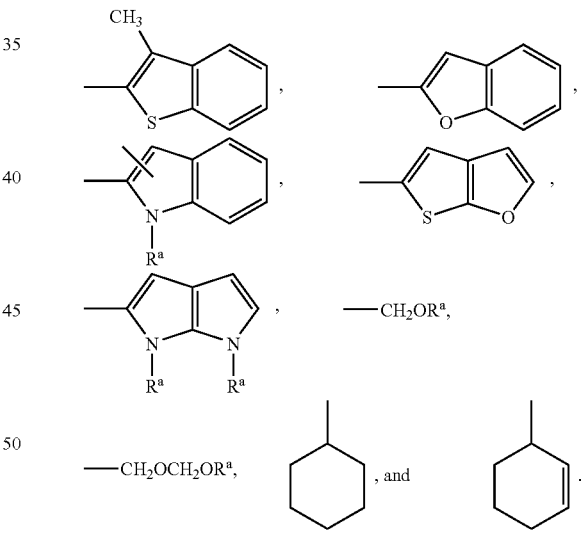

Within this particular group of compounds, preferred $R^a$ substituents include hydrogen, $C_{1-6}$alkyl, and benzyl.

In a preferred embodiment, $R^2$ is selected from the group consisting of hydrogen, aryl, heteroaryl, $OR^a$, $NR^aR^b$, $NR^bR^c$, $C_{1-4}$alkyleneHet, $C_{1-4}$alkyleneheteroaryl, $C_{1-4}$alkylenearyl, $C_{1-4}$alkyleneC(=O)$C_{1-4}$alkylenearyl, $C_{1-4}$alkyleneC(=O)$OR^a$, $C_{1-4}$alkyleneC(=O)$NR^bR^c$, $C_{1-4}$alkyleneC(=O)Het, $C_{1-4}$alkyleneNR$^b$R$^c$, $C_{1-4}$alkyleneNR$^a$C(=O)$R^a$, and $C_{1-4}$alkyleneO$C_{1-4}$alkyleneOR$^a$. In a more preferred embodiment, $R^2$ is hydrogen.

In preferred embodiments, $R^3$ is hydrogen, $C_{1-6}$alkyl, aryl, or heteroaryl.

In preferred embodiments, Y is null, or is C(=O), C(=O)C≡C, C(=O)(CH$_2$)$_t$, SO$_2$, or C(=S).

In preferred embodiments, A is selected from the group consisting of

phenyl

furanyl

thienyl

pyrrolyl

oxazolyl

thiazolyl

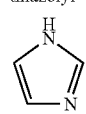
imidazolyl

pyrazolyl

isoxazolyl

isothiazolyl

1, 2, 3-oxadiazolyl

1, 2, 3-triazolyl

-continued

1, 3, 4-thiadiazolyl

1, 2, 4-oxadiazolyl

1, 2, 5-oxadiazolyl

1, 3, 4-oxadiazolyl

1, 2, 3, 4-oxatriazolyl

1, 2, 3, 5-oxatriazolyl

pyridinyl

pyridazinyl

pyrimidinyl

pyrazinyl

1, 3, 5-triazinyl

1, 2, 4-triazinyl

1, 2, 3-triazinyl

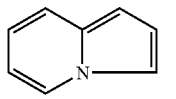
indolizinyl

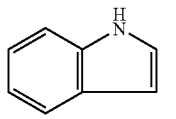
indolyl

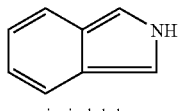
isoindolyl

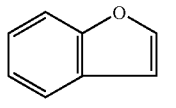
benzo (b) furanyl

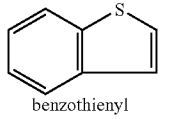
benzothienyl

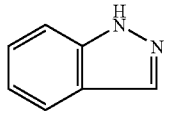
1H-indazolyl

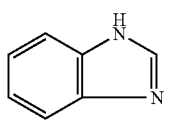
benzmidazolyl

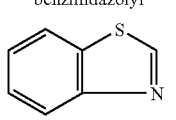
benzthiazonyl

purinyl

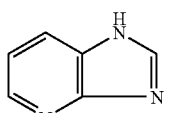
purinyl

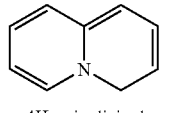
4H-quionlizinyl

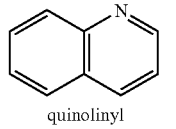
quinolinyl

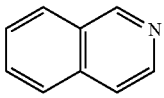
isoquinolinyl

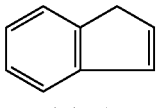
indenyl

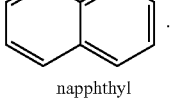
napphthyl $R^4$ is selected from the group consisting of hydrogen, $C_{1-6}$alkyl, aryl, heteroaryl, halo, $C(\!=\!O)OR^b$, $NHC(\!=\!O)C_{1-3}$ alkyleneN$(R^b)_2$, $NO_2$, $C(\!=\!O)OR^b$, $OR^b$, $CF_3$, $OR^a$, CN, $OC(\!=\!O)R^b$, arylOR$^b$, Het, $NR^aC(\!=\!O)C_{1-3}$alkyleneC$(\!=\!O)OR^a$, arylOC$_{1-3}$alkyleneNR$^a$R$^b$, arylOC$(\!=\!O)R^a$, $C_{1-4}$alkyleneC$(\!=\!O)OR^b$, $OC_{1-4}$alkyleneC$(\!=\!O)OR^b$, $C(\!=\!O)NR^bSO_2R^c$, $C_{1-4}$alkyleneNR$^b$R$^c$, $C_{2-6}$alkenyleneNR$^b$R$^c$, $C(\!=\!O)NR^bC_{1-4}$alkyleneOR$^b$, NR$^b$C$_{1-4}$alkyleneNR$^b$R$^c$, NR$^b$C$(\!=\!O)R^c$, NR$^b$C$(\!=\!O)NR^bR^c$, $OSO_2CF_3$, $C(\!=\!O)R^b$, $C_{1-3}$alkylenearyl, $C_{1-4}$alkyleneHet, $C_{1-6}$alkyleneOR$^b$, $C_{1-3}$alkyleneN$(R^b)_2$, NR$^b$R$^c$, $C(\!=\!O)NR^bR^c$, NHC$(\!=\!O)C_1$–$C_3$alkylenearyl, $C_{3-8}$cycloalkyl, $C_{3-8}$heterocycloalkyl, NHC$(\!=\!O)C_{1-3}$alkyleneHet, NHC$(\!=\!O)$haloC$_{1-6}$alkyl, and

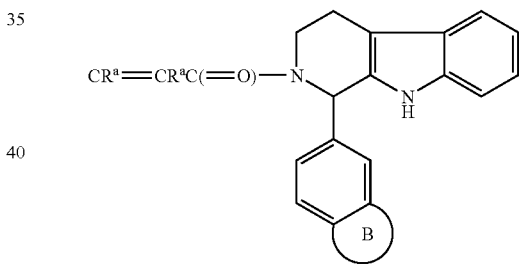

In preferred embodiments, p is 0 or $R^5$ groups, independently, are selected from the group consisting of halo, oxo, $C_{1-6}$alkyl, NR$^a$R$^b$, or OR$^a$.

In especially preferred embodiments, q is 0 or $R^0$ is selected from the group consisting of halo, methyl, trifluoromethyl, and trifluoromethoxy; $R^1$ is selected from the group consisting of

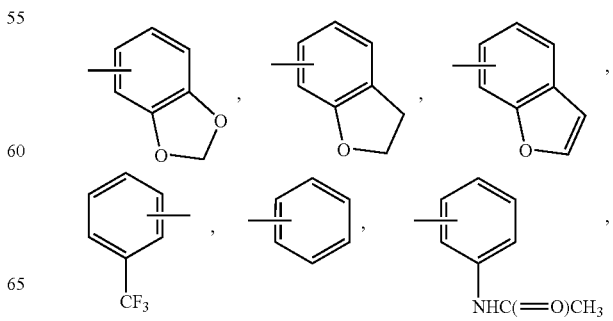

-continued

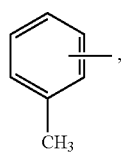 , 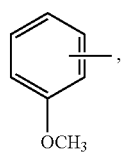 , 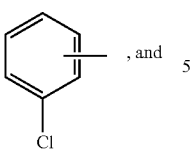 , and

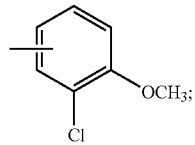 ;

R² is selected from the group consisting of hydrogen, C₁₋₆alkyl, C(=O)NR^bR^c, and C₁₋₄alkyleneHet; R³ is selected from the group consisting of hydrogen, C₁₋₆alkyl, aryl, and heteroaryl; Y is null, or Y is selected from the group consisting of selected from the group consisting of C(=O), C(=O)C≡C, C(=O)CH₂, C(=O)CH₂CH₂, and SO₂; A is selected from the group consisting of

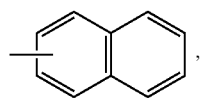 , 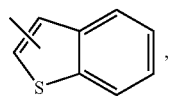 ,

 , 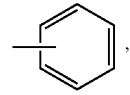 ,

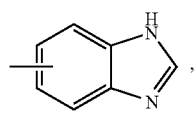 , 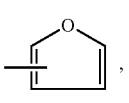 ,

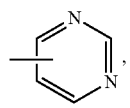 , 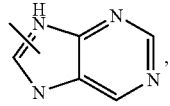 ,

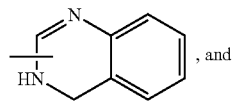 , and 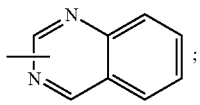 ;

R⁴ is selected from the group consisting of H, NHC(=O)CH₃, N(CH₃)₂, C(=O)NH₂, NHCH₃, NO₂, NH₂, Br, C(=O)CH₃, OCH₃, CH₂OCH₃, NHC(=O)CH₂N(CH₃)₂, CH₂N(CH₃)₂, CH₃, Cl, NHC(=O)CH₂CO₂H,

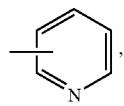 , 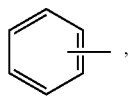 ,

-continued

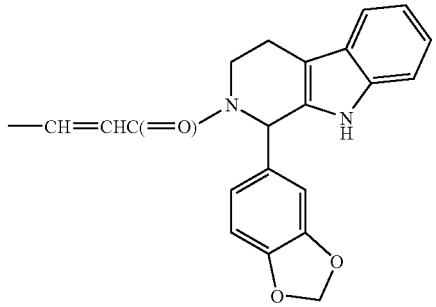 ,

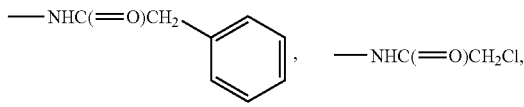 ,

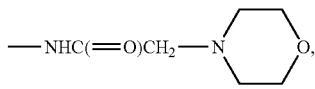 , —NHC(=O)CH₂Cl,

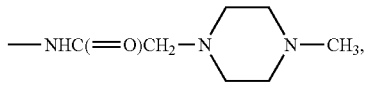 ,

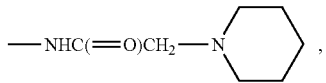 ,

 ,

—NHC(=O)CH₂C(=O)OCH₃,

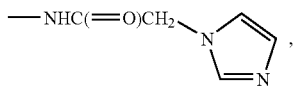 ,

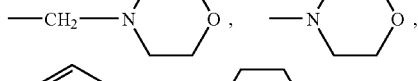 ,

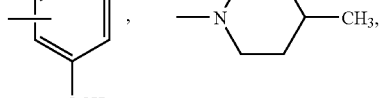 ,

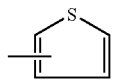 ,

 ,

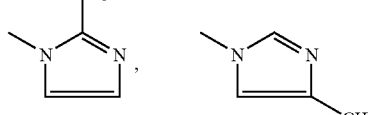 ,

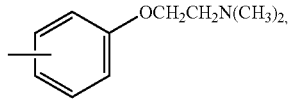 ,

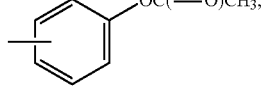 ,

-continued

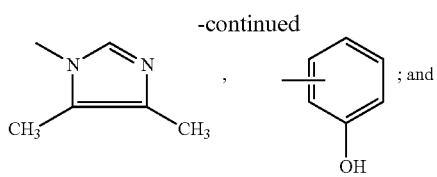, and p is 0 or $R^5$ groups, independently, are selected from the group consisting of $CH_3$, Cl, oxo, and $OCH_3$.

An especially preferred subclass of compounds within the general scope of formula (I) is represented by compounds of formula (III)

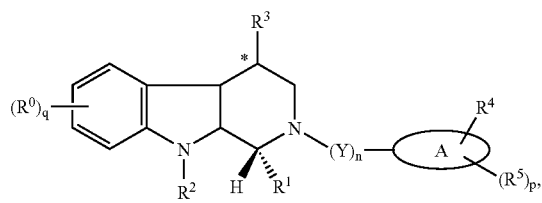

(III)

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, $R^3$, $R^4$, and $R^5$, as well as Y and A, are defined as in structural formula (I) above. For example, compounds of structural formula (I) can be prepared according to the following synthetic scheme, which comprises reacting compounds of formulae (IV) and (V). This type of reaction is described in Bombrun U.S. Pat. No. 6,117,881, incorporated herein by reference.

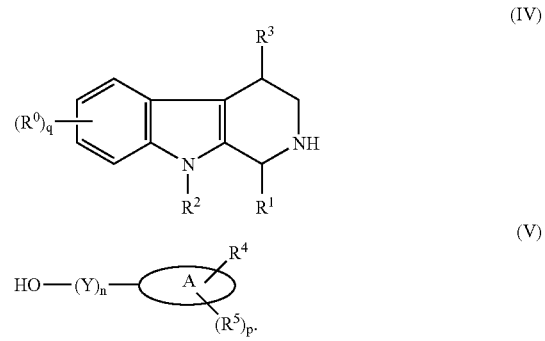

The reaction is performed in the presence of 1-(3-dimethylaminopropyl)-3-ethylcarbodiimide hydrochloride (EDCI) and 1-hydroxybenzotriazole (HOBT) in a suitable organic solvent, such as dimethylformamide (DMF) or dichloromethane ($CH_2Cl_2$) for several hours, e.g., 8 hours to 2 days.

A compound of formula (IV) can be prepared by Pictet-Spengler cyclization between a tryptamine derivative of formula (VI) and an aldehyde of formula $R^1CHO$.

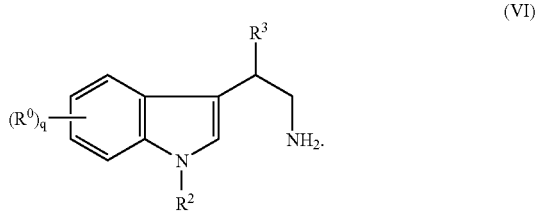

The reaction can be performed in a suitable solvent such as a halogenated hydrocarbon (e.g., dichloromethane) or an aromatic hydrocarbon (e.g., toluene) in the presence of an acid, such as trifluoroacetic acid (TFA). The reaction can be performed at a temperature of 20° C. to reflux to provide a compound of formula (IV) in one step. The reaction also can be carried out in a solvent, such as an aromatic hydrocarbon (e.g., toluene), under reflux, optionally using a Dean-Stark apparatus to trap the produced water.

The reaction provides racemic compounds of formula (IV). Enantiomers can be obtained from a resolution of N-acetyl leucine using fractional crystallization in EtOAc: MeOH (ethyl acetate:methanol) as the solvent. (R) and (S) enantiomers can be isolated as salts, depending upon whether N-acetyl-(D)- and -(L)-leucine was used as the starting material.

Compounds of formulae (VI) and $R^1$CHO are commercially available compounds or are prepared by standard synthetic techniques.

The following examples show other synthetic methods for the preparation of compounds of structural formula (I).

It should be understood that protecting groups can be utilized in accordance with general principles of synthetic organic chemistry to provide compounds of structural formula (I). Protecting group-forming reagents, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

In addition, compounds of formula (I) can be converted to other compounds of formula (I). Thus, for example, a particular R substituent can be interconverted to prepare another suitably substituted compound of formula (I). Examples of appropriate interconversions include, but are not limited to, $OR^a$ to hydroxy by suitable means (e.g., using an agent such as $BBr_3$ or a palladium catalyst, like palladium-on-carbon, with hydrogen), or amino to substituted amino, such as acylamino or sulphonylamino, using standard acylating or sulfonylating conditions.

Compounds of formula (I) can be prepared by the method above as individual stereoisomers or as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization, from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following additional abbreviations are used hereafter in the accompanying examples: rt (room temperature), min (minute), h (hour), g (gram), mmol (millimole), m.p. (melting point), eq (equivalents), L (liter), mL (milliliter), μL (microliter), saturated (sat.), DMSO (dimethyl sulfoxide), $CH_2Cl_2$ (dichloromethane), IPA (isopropyl alcohol), TFA (trifluoroacetic acid), EtOH (ethanol), MeOH (methanol), DMF (dimethylformamide), $CHCl_3$ (chloroform), NaOH (sodium hydroxide), $Na_2SO_4$ (sodium sulfate), $Et_2O$ (diethyl ether), EtOAc (ethyl acetate), $Na_2CO_3$ (sodium carbonate), $MgSO_4$ (magnesium sulfate), $iPr_2O$ (diisopropyl ether), $NaHCO_3$ (sodium bicarbonate), $Et_3N$ (triethylamine), AcOH (acetic acid), and THF (tetrahydrofuran).

Intermediate 1

1-Phenyl-2,3,4,9-tetrahydro-1H-β-carboline

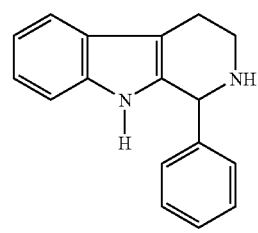

A solution of tryptamine (15 g, 94.0 mmol) and benzaldehyde (10.9 g, 1.1 eq.) in $CH_2Cl_2$ (800 mL) was treated with TFA (15 mL, 2 eq.). The resulting mixture was stirred at room temperature (rt) for one day, then neutralized to pH 7 with a saturated aqueous solution of $Na_2CO_3$. After filtration and concentration to dryness, the residue was recrystallized from IPA to give Intermediate 1 (11.0 g, 47%) as white crystals (m.p.: 175–177° C.).

Intermediate 2

1-(3,4-Methylenedioxyphenyl)-2,3,4,9-tetrahydro-1H-β-carboline

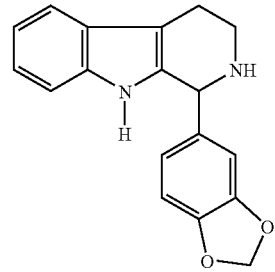

Intermediate 2 was prepared by the same procedure as Intermediate 1 using tryptamine (20.0 g, 120 mmol), 3,4-methylenedioxybenzaldehyde (20.6 g, 1.1 eg.) and TFA (18 mL, 2 eq.) to give Intermediate 2 (22 g, 60%) as white crystals after recryslatllizatoin from ethanol (m.p.: 178° C.).

Intermediate 3

1-(2,3-Dihydrobenzofuran-5-yl)-2,3,4,9-tetrahydro-1H-β-carboline

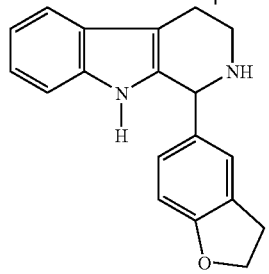

Intermediate 3 was prepared using a two-step procedure. A solution of tryptamine (32.4 g, 0.2 mol) and 2,3-dihydrobenzofuran-5-carboxaldehyde (30.0 g, 1 eq.) in toluene (1 L) was heated under reflux for 4 hours. After removal of 4 mL of water and evaporation of toluene, the residue was dissolved in $CH_2Cl_2$ (1 L) in the presence of TFA (31 mL, 2 eq.). The resulting mixture was stirred at rt for 16 hours. Then, 1 L of a saturated aqueous solution of $NaHCO_3$ was added. After extraction with $CH_2Cl_2$ and drying over $MgSO_4$, the organic solution was evaporated in vacuo. Recrystallization from $CH_2Cl_2/iPr_2O$ (2:30) gave the title compound as white crystals in an 80% yield. $^1$H NMR ($CDCl_3$), δ 7.6 (s, 1H), 7.5–7.6 (m, 1H), 7–7.3 (m, 5H), 6.7–6.75 (d, 1H), 5.1 (s, 1H), 4.5–4.6 (t, 2H), 3.3–3.45 (m, 1H), 3.05–3.2 (t, 3H), 2.7–3 (m, 2H).

Intermediate 4

(R)-1-(2,3-Dihydrobenzofuran-5-yl)-2,3,4,9-tetrahydro-1H-β-carboline

Resolution of the racemic Intermediate 3 was achieved using N-acetyl-(D)-leucine (Sigma) in MeOH:EtOAc followed by recrystallization from MeOH. The suspension of the recrystallized material in $CH_2Cl_2$ was treated with a sat. aqueous $NaHCO_3$ to give the enantiomerically pure Intermediate 4 in 55% yield (m.p.: 98–99° C.).

Analysis for $C_{19}H_{18}N_2O.0.15H_2O$: Calculated: C, 77.87; H, 6.29; N, 9.56. Found: C, 77.83; H, 6.33; N, 9.44. $[α]_D^{21}$=+42° (c=0.5, MeOH).

Intermediates 5 and 6 were prepared from Intermediate 2 and the appropriate carboxylic acid or acid chloride. Intermediate 7 was prepared from benzylamine and terephthalic acid.

Intermediate 5

(E)-1-(1-Benzo[1,3]dioxol-5-yl-1,3,4,9-tetrahydro-β-carbolin-2-yl)-3-(2-nitrophenyl)propenone

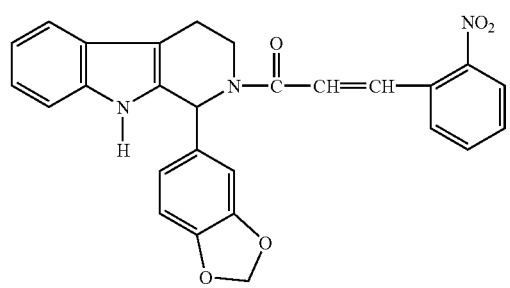

Intermediate 6

4-[1-(1-Benzo[1,3]dioxol-5-yl-1,3,4,9-tetrahydro-β-carbolin-2-yl)methanolyl]benzoic acid methyl ester

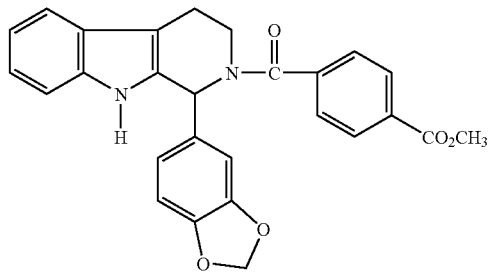

Intermediate 7

N-Benzylterephthalamic acid

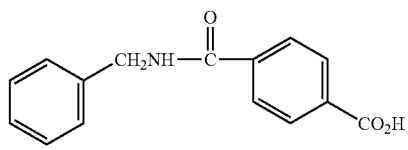

EXAMPLE 1

1-(2H-Benzo[d]1,3-dioxolan-5-yl)(1,2,3,4-tetrahydro-β-carbolin-2-yl)-2-naphthyl ketone

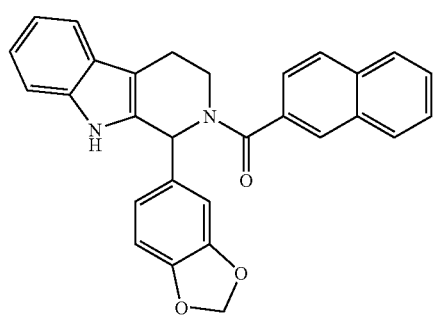

Naphthalene-2-carbonyl chloride was added to Intermediate 2 to provide Example 1 in 75% yield: mp 248–249° C. $^1$H NMR (DMSO-$d_6$) δ: 11.1 (s, 0.2H), 11.08 (s, 0.8H), 8.06–7.95 (m, 2H), 7.74–7.24 (m, 7H), 7.15–6.76 (m, 6H), 6.15 (s, 2H), 3.47–3.17 (m, 2H), 2.85–2.40 (m, 2H); MS ES+m/e 447 (p+1), ES−m/e 445 (m−1); IR (KBr, cm$^1$): 3282, 1617, 1633.

EXAMPLE 2

1-(2H-benzo[d]1,3-dioxolan-5-yl)(1R)(1,2,3,4-tetrahydro-β-carbolin-2-yl)2-naphthyl ketone

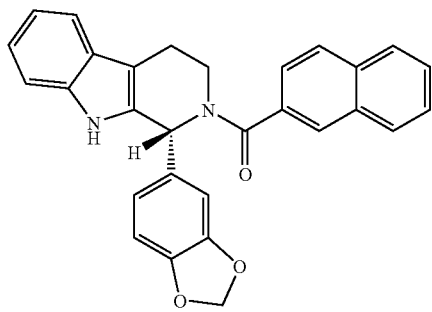

Naphthalene-2-carbonyl chloride was added to the (1R) stereoisomer of Intermediate 2 to provide Example 2 in 74% yield. mp 285° C. $^1$H NMR (DMSO-d$_6$) δ: 11.1 (s, 0.2H), 11.08 (s, 0.8H), 8.06–7.95 (m, 2H), 7.74–7.24 (m, 7H), 7.15–6.76 (m, 6H), 6.15 (s, 2H), 3.47–3.17 (m, 2H), 2.85–2.40 (m, 2H); MS ES+m/e 447 (p+1), ES−m/e 445 (p−1); IR (KBr, cm$^{-1}$): 3282, 1617, 1633; 100% ee.

EXAMPLE 3

1-(1-Benzo[1,3]dioxol-5-yl-1,3,4,9-tetrahydro-β-carbolin-2-yl)-1-phenylmethane

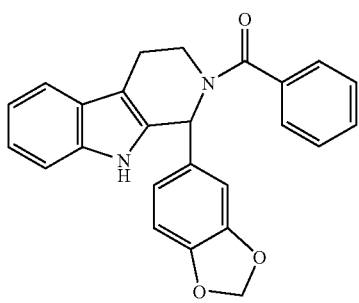

Intermediate 2 (0.68 mole, 200 mg) was reacted with benzoyl chloride (1.5 eq.) and NaHCO$_3$ (1.1 eq.) in CH$_2$Cl$_2$ by stirring the reaction mixture at room temperature. The reaction was quenched with aqueous sat. NaHCO$_3$. The resulting mixture was extracted with CH$_2$Cl$_2$, and the organic phase was dried. After filtering and removing the solvent by evaporation, Example 3 was purified by flash chromatography, eluting with CH$_2$Cl$_2$. The product was recrystallizated from EtOH/CH$_2$Cl$_2$ (3/1) to provide Example 3 as white crystals. (m.p. 260–261° C.), m.w. 396.45 (C$_{25}$H$_{20}$N$_2$O$_3$).

EXAMPLE 4

N-{4[1-(1-Benzo[1,3]dioxol-5-yl-1,3,4,9-tetrahydro-β-carboline-2-yl)-methanoyl]phenyl}acetamide

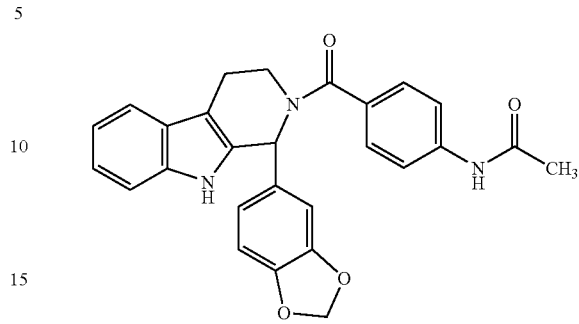

Intermediate 2 was reacted with 4-acetamidobenzoic acid in CH$_2$Cl$_2$ in the presence of EDCI and Et$_3$N. The reaction product was isolated and purified by flash chromatography, eluting with CH$_2$Cl$_2$/MeOH (98:2). Recrystallization from ethanol yielded Example 4 as a white solid. m.p. 186–188° C., m.w. 453.5 (C$_{27}$H$_{23}$N$_3$O$_4$).

EXAMPLE 5

1-(1-Benzo[1,3]dioxol-5-yl-1,3,4,9-tetrahydro-β-carbolin-2-yl)-1-(4-methylaminophenyl)methanone

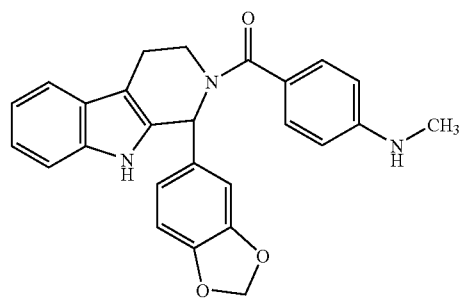

Intermediate 2 was reacted with 4-(methylamino)benzoic acid in CH$_2$Cl$_2$ in the presence of EDCI and Et$_3$N. The reaction product was isolated and purified. Recrystallization yielded Example 5 as a white solid. m.w. 425.45 (C$_{26}$H$_{23}$N$_3$O$_3$).

EXAMPLE 6

1-(1-Benzo[1,3]dioxol-5-yl-1,3,4,9-tetrahydro-β-carbolin-2-yl)-1-(4-dimethylaminophenyl)methanone

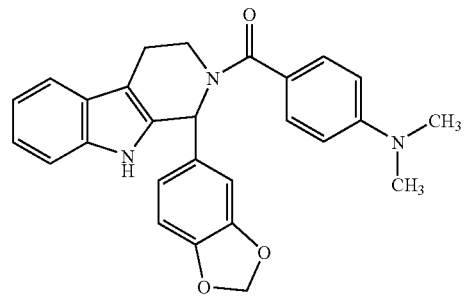

Intermediate 2 was reacted with 4-(dimethylamino)benzoic acid in $CH_2Cl_2$ in the presence of EDCI and $Et_3N$. The reaction product was isolated and purified. Recrystallization from $CH_2Cl_2$ yielded Example 6 as a white solid. m.w. 439.12 ($C_{27}H_{25}N_3O_3$).

EXAMPLE 7

4-[1-(1-Benzo[1,3]dioxol-5-yl-1,3,4,9-tetrahydro-β-carbolin-2-yl)methanoyl]benzamide

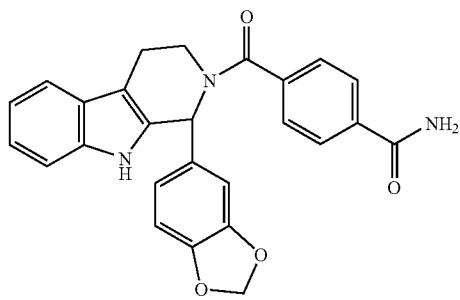

Intermediate 6 was dissolved in 100 mL of $CH_3OH$, then reacted with ammonia at 35° C. for about 2 hours. The $CH_3OH$ was evaporated, and the residue was extracted with $CH_2Cl_2$, followed by washing with brine. After drying, the $CH_2Cl_2$ was removed to yield Example 7. m.w. 439.47 ($C_{26}H_{21}N_3O_4$).

EXAMPLE 8

1-(1-Benzo[1,3]dioxol-5-yl-1,3,4,9-tetrahydro-β-carbolin-2-yl)-3-phenylpropynone

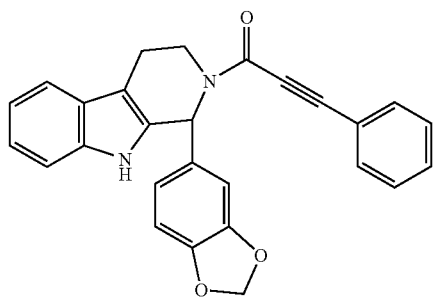

Intermediate 2 was reacted with 3-phenylpropyne carboxylic acid in $CH_2Cl_2$ in the presence of HOBT, EDCI, and $Et_3N$. The reaction product was isolated and purified by flash chromatography, eluting with $CH_2Cl_3$. Recrystallization from EtOH yielded Example 8 as a white solid. m.p. 145.6° C., m.w. 420.47 ($C_{27}H_{20}N_2O_3$).

EXAMPLE 9

3-(2-Aminophenyl)-1-(1-benzo[1,3]dioxol-5-yl-1,3,4,9-tetrahydro-β-carbolin-2-yl)propan-1-one

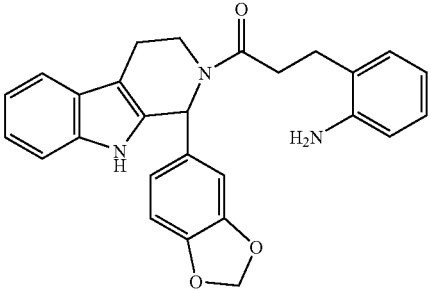

Intermediate 5 was hydrogenated in the presence of a Pd/C (palladium on carbon) catalyst in a 50/50 mixture of EtOH/THF. The reaction was allowed to proceed for four hours, followed by filtering of the Pd/C catalyst from the reaction mixture, and removing the solvents by evaporation. The resulting product was extracted with $CH_2Cl_2$, which then was removed by evaporation. The reaction product was purified by chromatography, eluting with $CH_2Cl_2$. The product was recrystallized from a water/IPA solution to yield Example 9 as a white solid. (m.p. 214° C.), m.w. 439.52 ($C_{27}H_{25}N_3O_3$).

EXAMPLE 10

N-{4-[1-(1-Benzo[1,3]dioxol-5-yl-1,3,4,9-tetrahydro-β-carbolin-2-yl)methanoyl]phenyl}-2-phenylacetamide

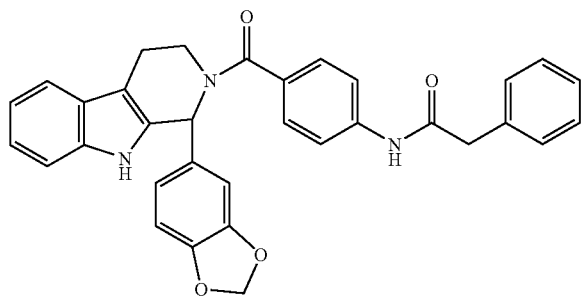

Intermediate 2 was reacted with Intermediate 7 in $CH_2Cl_2$ in the presence of HOBT, EDCI, and $Et_3N$. The reaction product was isolated and purified by flash chromatography, eluting with $CH_2Cl_2$/MeOH (95:5). Recrystallization from EtOH/water yielded Example 10 as a white solid. (m.p. 151–152° C.), m.w. 529.60 ($C_{33}H_{27}N_3O_4$).

EXAMPLE 11

1-(1-Benzo[1,3]dioxol-5-yl-1,3,4,9-tetrahydro-β-carbolin-2-yl)-3-phenylpropan-1-one

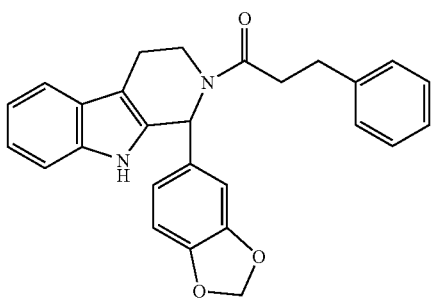

Intermediate 2 was reacted with 3-phenylpropanoic acid in $CH_2Cl_2$ in the presence of EDCI, HOBT, and $Et_3N$. The reaction product was isolated and purified. Recrystallization from $CH_3OH$ yielded Example 11 as a white solid. m.w. 424.50 ($C_{27}H_{21}N_2O_3$).

To a solution of Intermediate 2 (0.20 g., 0.68 mmol) and $CH_2Cl_2$ (100 mL) was added 5-benzimidazole carboxylic acid (0.12 g, 1.1 eq.), HOBT (0.12 g, 1.1 eq.), EDCI (0.14 g. 1.1 eq.), and $Et_3N$ (0.10 mL, 1.1 eq.) at 25° C. After stirring at rt until the reaction was complete, the reaction mixture was quenched with water (20 mL). The quenched reaction mixture was extracted with $CH_2Cl_2$, then the organic layer was washed with brine and dried over $MgSO_4$. The solvent was removed in vacuo, then the residue was purified by flash chromatography, eluting with $CH_2Cl_2$/MeOH (95:5). Recrystallization from EtOH yielded Example 12 as white crystals. m.w. 438.47 ($C_{26}H_{20}N_4O_3$).

Examples 13–22 were prepared in a manner similar to Example 1–12. Example 23 further illustrates the preparation of compounds of the present invention.

EXAMPLE 13a

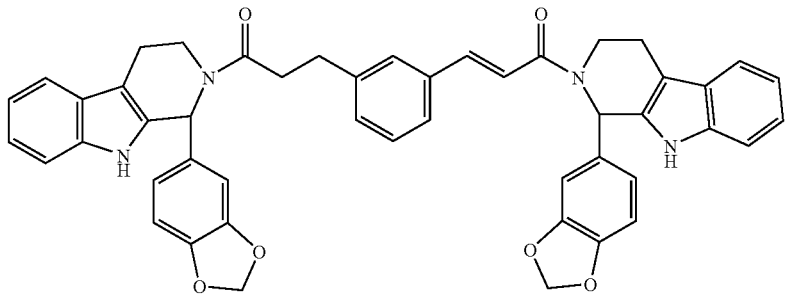

EXAMPLE 12

1-(1-Benzo[1,3]dioxol-5-yl-1,3,4,9-tetrahydro-β-carbolin-2-yl)-1-(3H-benzoimidazol-5-yl)methanone

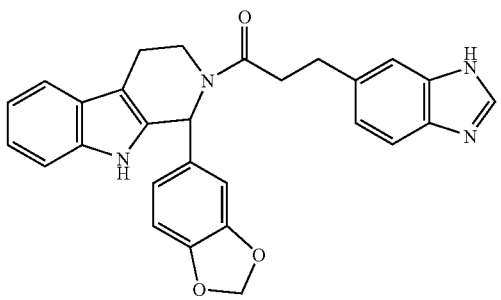

EXAMPLE 13b

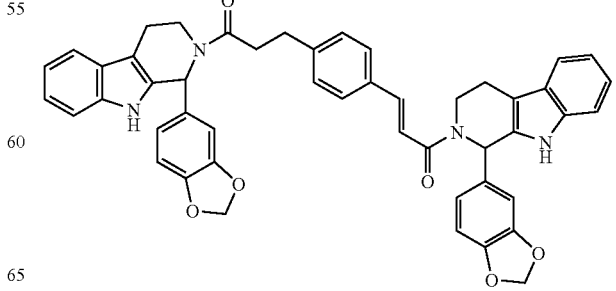

EXAMPLE 14
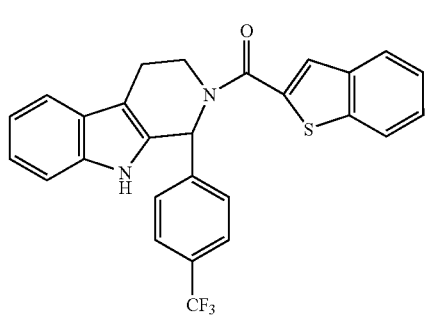
EXAMPLE 15
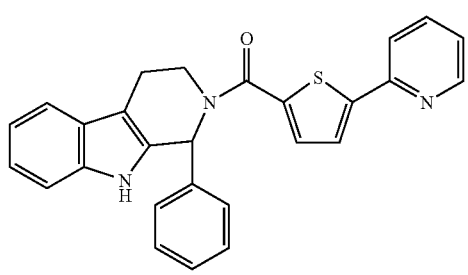
EXAMPLE 16
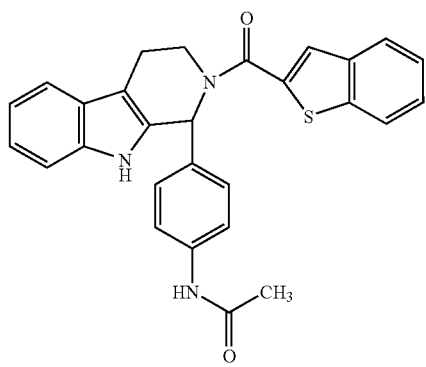
EXAMPLE 17
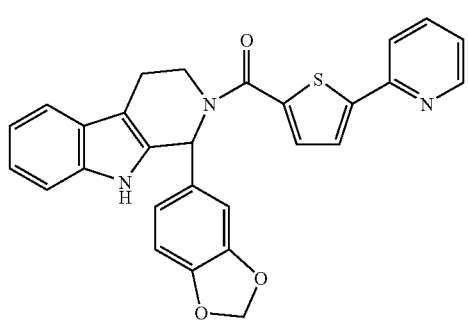
EXAMPLE 18
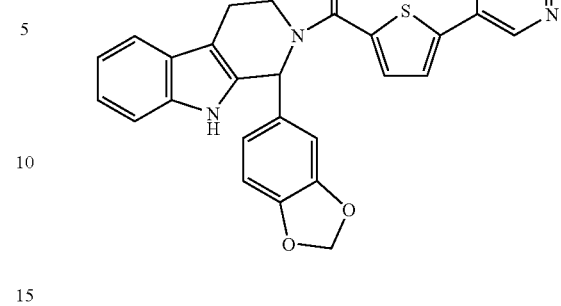
EXAMPLE 19
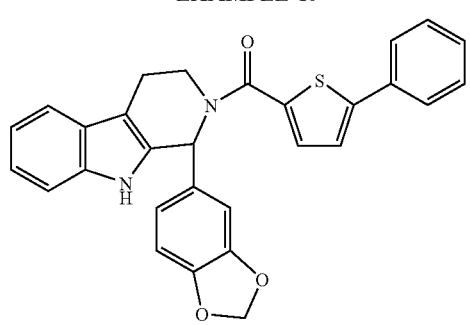
EXAMPLE 20
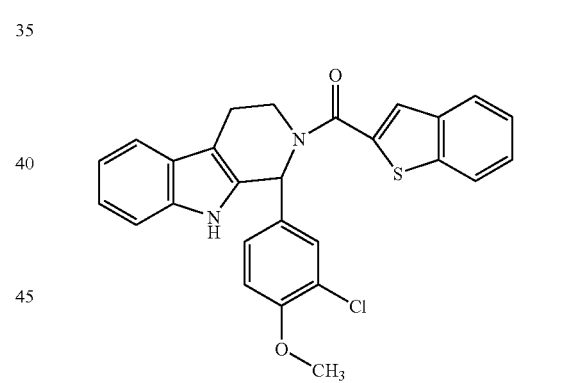
EXAMPLE 21
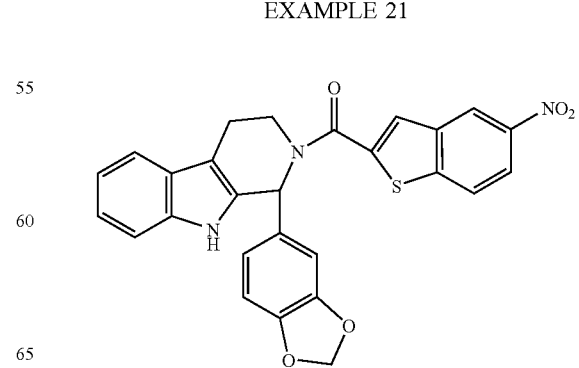

EXAMPLE 22

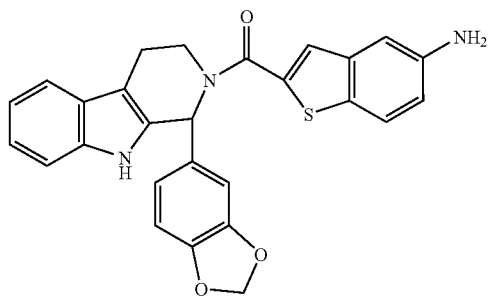

EXAMPLE 23

2-Benzo[b]thiophen-3-yl-1-(1-benzo[1,3]dioxol-5-yl-1,3,4,9-tetrahydro-β-carbolin-2-yl)ethanone

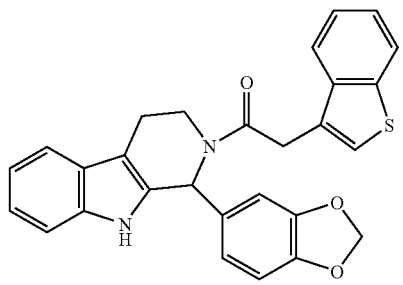

Intermediate 2 was reacted with 3-benzothiophene carboxylic acid in $CH_2Cl_2$ in the presence of HOBT, EDCI, and $Et_3N$. The reaction product was isolated and purified by flash chromatography, eluting with $CH_2Cl_2$/MeOH (90:10). Recrystallization from $iPr_2O$ yielded Example 23 as a white solid. m.w. 466.56 ($C_{28}H_{22}N_2O_3S$).

The following Examples 24–44 were prepared by synthetic procedures similar to the procedures used to prepare Examples 1–23.

EXAMPLE 24

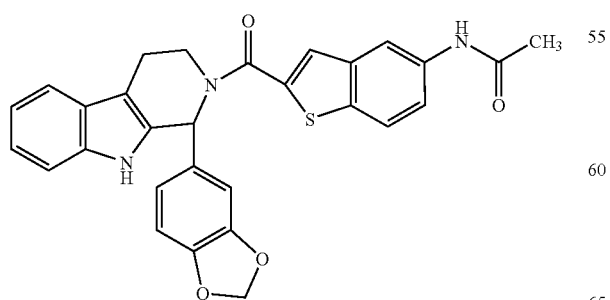

EXAMPLE 25

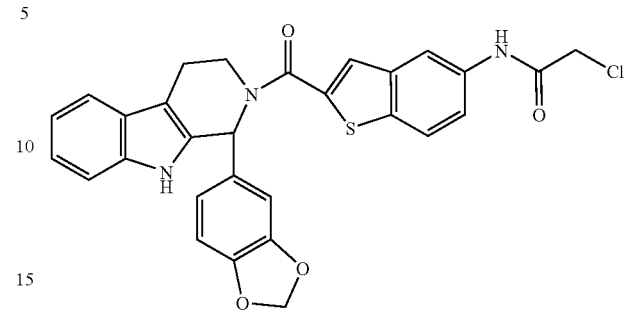

EXAMPLE 26

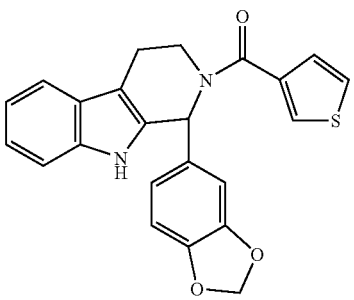

EXAMPLE 27

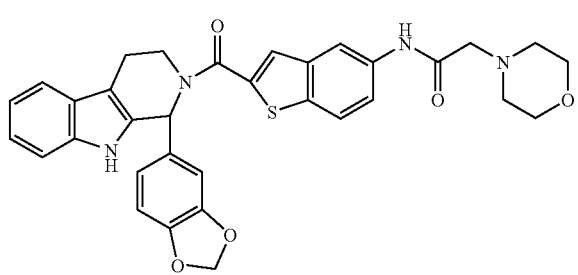

EXAMPLE 28

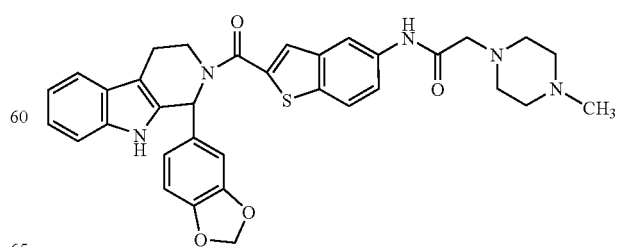

EXAMPLE 29
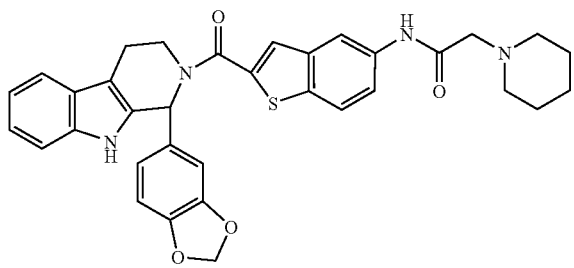
EXAMPLE 30
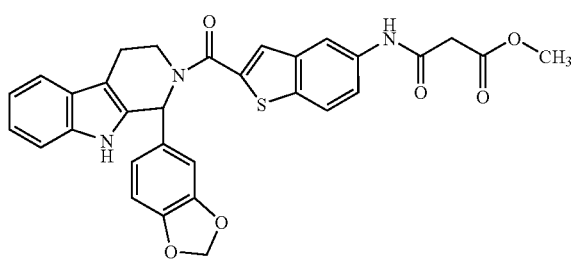
EXAMPLE 31
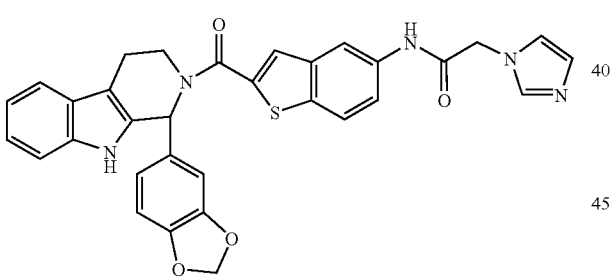
EXAMPLE 32
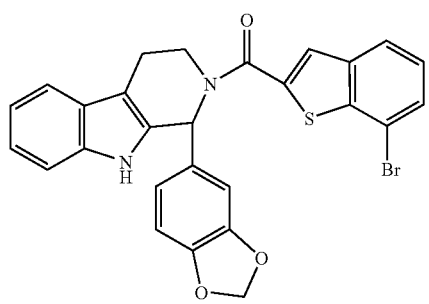
EXAMPLE 33
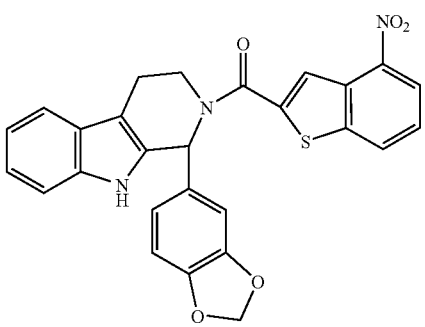
EXAMPLE 34
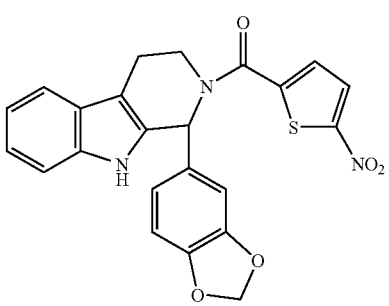
EXAMPLE 35
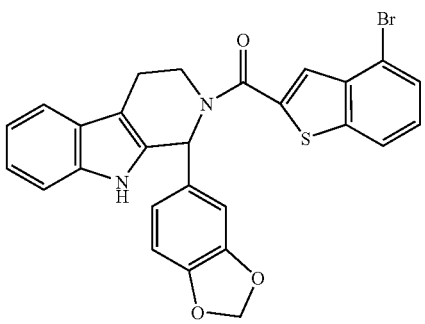

EXAMPLE 36
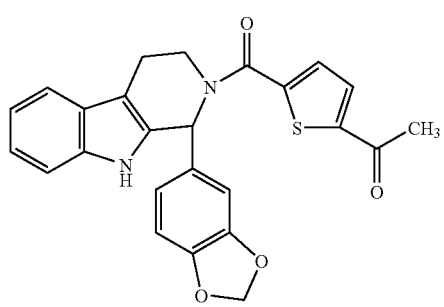
EXAMPLE 37
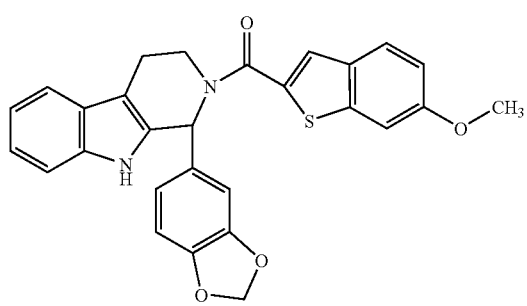
EXAMPLE 38
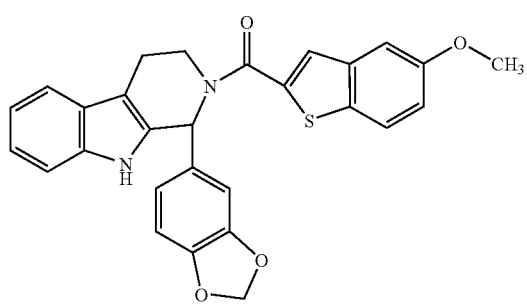
EXAMPLE 39
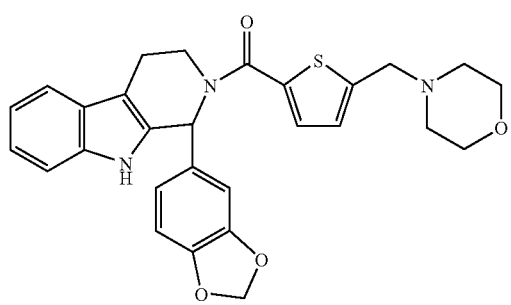
EXAMPLE 40
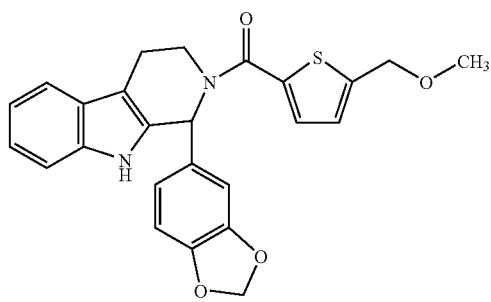
EXAMPLE 41
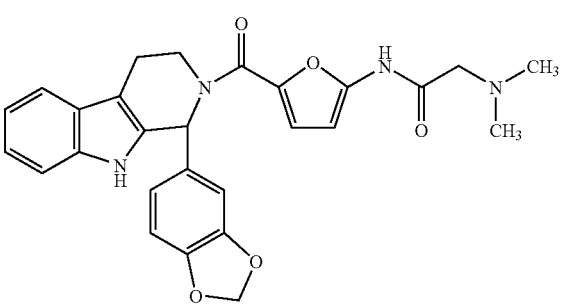
EXAMPLE 42
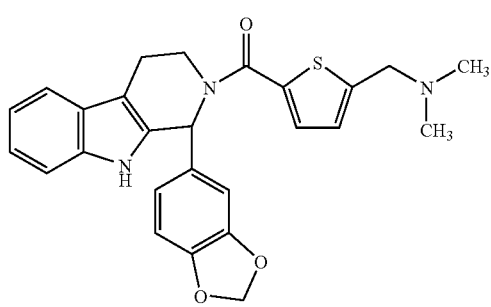
EXAMPLE 43
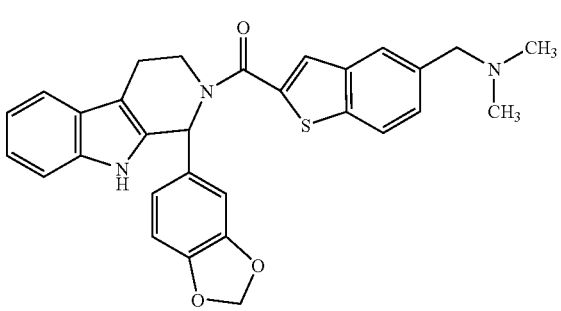

EXAMPLE 44

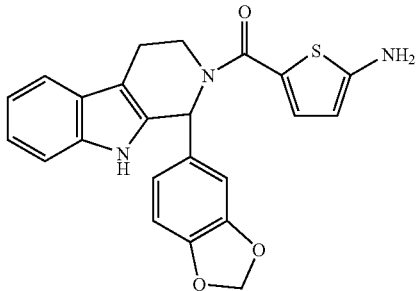

EXAMPLE 45

2-[(1-(2H-benzo[d]1,3-dioxolan-5-yl)-(1R)-(1,2,3,4-tetrahydro-β-carbolin-2-yl)sulfonyl]-5-chloro-3-methylbenzo[b]thiophene

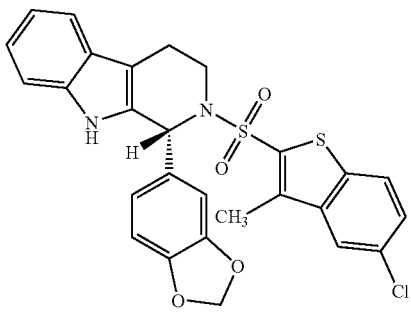

(5-Chloro-3-methylbenzothiophen-2-yl)-sulfonyl chloride was added to Intermediate 2 to provide Example 45 in 46% yield. mp 139–143° C. NMR (DMSO-d$_6$) δ: 10.9 (s, 1H), 8.03 (d, J=8.8 Hz, 1H), 7.93 (s, 1H), 7.53 (dd, J=2.0, 8.7 Hz, 1H), 7.30 (m, 2H), 7.09 (m, 1H), 6.85–6.95 (m, 2H), 6.70 (s, 1H), 6.62 (dd, J=1.5, 8.0 Hz), 6.25 (s, 1H), 6.00 (s, 1H), 5.99 (s, 1H), 4.05 (dd, J=5.3, 14.5 Hz, 1H), 3.38–3.40 (m, 1H), 2.70 (dd, J=3.8, 16 Hz), 2.41–2.44 (m, 1H), 2.40 (s, 3H); MS ES+m/e 537.1 (p+1) E/S–m/e 535.1 (p–1).

EXAMPLE 46

2-(1-Benzo[1,3]dioxol-5-yl-1,3,4,9-tetrahydro-β-carbolin-2-yl)-6,7-dimethoxy-3H-quinazolin-4-one

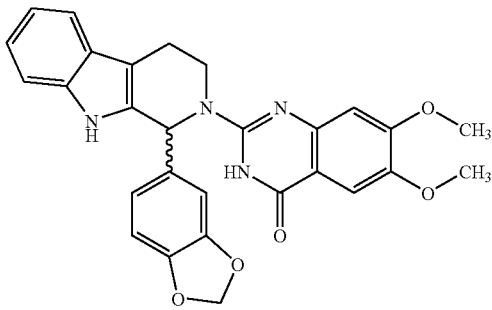

Example 46 was prepared from Intermediate 2 and the quinazoline Intermediate 8 by the following synthetic procedure. Intermediate 8 was prepared in accordance with the procedure set forth in J. Miller et al., *J. Med. Chem.*, 28, p. 12 (1985).

Quinazolinone Intermediate 8

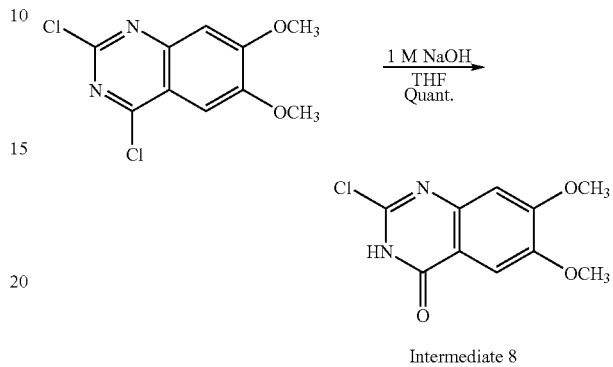

Intermediate 8

A solution of 2,4-dichloro-6,7-dimethoxy-quinazoline (2.12 g, 8.20 mmol) in 1 M NaOH (50 mL) and THF (15 mL) was stirred at room temperature under an argon blanket for 23 hours. The solution was cooled to 0° C., then acidified to pH 5 with AcOH. The resulting solids were collected by vacuum filtration and dried in a vacuum oven at 70° C. overnight to provide Intermediate 8 as a pale yellow powder (2.02 g, 100%). $^1$H NMR (300 MHz, DMSO-d$_6$) δ: 7.38 (s, 1H), 7.08 (s, 1H), 3.88 (s, 3H), 3.85 (s, 3H), 3.50–3.20 (br s, 1H).

Preparation of Example 46

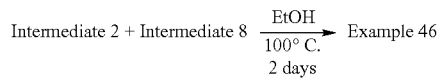

A suspension of Intermediate 2 (3.26 g, 11.2 mmol) and Intermediate 2 (1.69 g, 7.0 mmol) in EtOH (25 mL) was heated in a sealed tube at 110° C. for 2 days. The resulting solids were collected by vacuum filtration, then dissolved in EtOAc (100 mL). The mixture was washed with 1 M NaOH (100 mL), water (100 mL), and brine (100 mL), dried over Na$_2$SO$_4$, and filtered. The solvent was removed under reduced pressure to provide a yellow foam which was purified by flash column chromatography, eluting with EtOAc/CH$_2$Cl$_2$/MeOH (1:4:0.1), to provide the crude product as a yellow solid. This crude product was purified by a slurry in Et$_2$O/MeOH, followed by vacuum filtration to provide Example 46 as a white solid (1.03 g, 33%): mp 282–290° C.; TLC R$_f$ (4:1:0.1 CH$_2$Cl$_2$/EtOAc/MeOH=0.36. $^1$H NMR (300 MHz, DMSO-d$_6$) δ: 11.46 (s, 1H), 10.99 (s, 1H), 7.46 (d, J=7.53 Hz, 1H), 7.32–7.28 (m, 2H), 7.10–6.96 (m, 3H), 6.88–6.71 (m, 4H), 5.98 (d, J=3.74 Hz, 2H), 4.46 (m, 1H), 3.86 (s, 3H), 3.79 (s, 3H), 3.40–3.30 (m, 2H), 2.87–2.74 (m, 2H); API MS m/z 497 [C$_{28}$H$_{24}$N$_4$P$_5$+H]$^+$. Anal. Calcd. for C$_{28}$H$_{24}$N$_4$O$_5$: C, 67.73; H, 4.87; N, 11.28. Found: C, 67.53; H, 5.08; N, 11.12.

EXAMPLE 47a

1-Benzo[1,3]dioxol-5-yl-2-(4-chloro-6,7-dimethoxyquinazolin-2-yl)-2,3,4,9-tetrahydro-1H-β-carboline

EXAMPLE 47b

1-Benzo[1,3]dioxol-5-yl-2-(6,7-dimethoxyquinazolin-2-yl)-2,3,4,9-tetrahydro-1H-β-carboline Examples 47a and 47b were prepared from Example 46 by the following synthetic sequence.

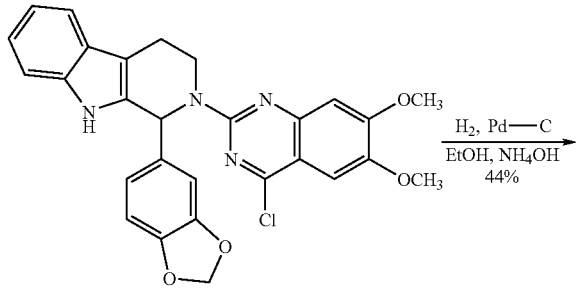

Example 47a

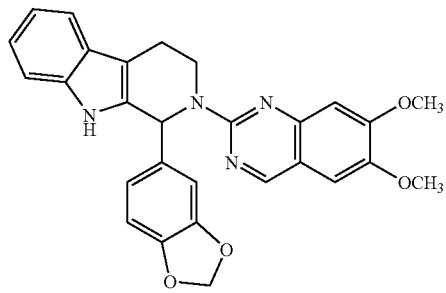

Example 47b

Preparation of Example 47a

Phosphorous oxychloride (0.41 mL, 4.4 mmol) was added slowly to a slurry of Example 46 (0.73 g, 1.5 mmol) and Et₃N (0.41 mL, 2.9 mmol) in 1,4-dioxane (10 mL), and the mixture was heated at 100° C. for 3 hours. The cooled reaction mixture was dissolved in CHCl₃ (100 mL), poured into ice water and neutralized with 2M NaOH. The organic layer was collected, washed with water (100 mL), and brine (100 mL), dried over Na₂SO₄, and concentrated under reduced pressure to provide an orange oil. This residue was purified by flash column chromatography, eluting with hexanes/EtOAc (2:1), to provide Example 47a as a yellow foam (0.80 g, 100%). A sample of Example 47a was further purified by a slurry in CH₂Cl₂, followed by vacuum filtration to provide a pale yellow solid which was dried overnight under vacuum at 85° C.: mp 231/234° C.; TLC $R_f$ (2:1 hexanes/ethyl acetate)=0.49. ¹H NMR (300 MHz, DMSO-d₆) δ: 10.98 (s, 1H), 7.46 (d, J=7.7 Hz, 1H), 7.31 (d, J=7.8 Hz, 1H), 7.17 (s, 1H), 7.10–6.97 (m, 3H), 6.90–6.86 (m, 2H), 6.79 (d, J=7.9 Hz, 1H), 5.97 (d, J=4.4 Hz, 2H), 4.93–4.89 (m, 1H), 3.95 (s, 3H), 3.88 (s, 3H), 3.27–3.23 (m, 2H), 2.86–2.85 (m, 2H) ppm; API MS m/z 515 [C₂₈H₂₃ClN₄O₄+H]⁺. Anal. Calcd. for C₂₈H₂₃ClN₄O₄: C, 65.31; H, 4.50; N, 10.88. Found: C, 64.92; H, 4.50; N, 10.79.

Preparation of Example 47b

A mixture of Example 47a (0.52 g, 1.01 mmol), a catalytic amount of 10% palladium on activated carbon (0.32 g, 10% wet), and concentrated ammonium hydroxide (1.5 mL) in EtOH (55 mL) was stirred under a hydrogen atmosphere for 12 hours at room temperature. The palladium catalyst was removed by vacuum filtration through a plug of Celite, and the resulting filtrate was concentrated under reduced pressure and purified by flash column chromatography, eluting with hexanes/EtOAc (2:1), to provide the crude product. This crude product was further purified by trituration with a hexane/Et₂O/CH₂Cl₂ mixture to provide Example 47b as a pale yellow solid (0.21 g, 44%): mp 201–204° C.; TLC $R_f$ (2:1 hexanes/EtOAc)=0.26. ¹H NMR (300 MHz, DMSO-d₆) δ: 10.98 (s, 1H), 9.02 (s, 1H), 7.45 (d, J=7.6 Hz, 1H), 7.31 (d, J=7.9 Hz, 1H), 7.24–7.22 (m, 2H), 7.09–6.76 (m, 5H), 5.97 (d, J=4.8 Hz, 2H), 5.04–4.99 (m, 1H), 3.93 (s, 3H), 3.84 (s, 3H), 3.27–3.21 (m, 2H), 2.86–2.82 (m, 2H) ppm; API MS m/z 481 [C₂₈H₂₄N₄O₄+H]⁺. Anal. Calcd. for C₂₈H₂₄N₄O₄: C, 69.99; H, 5.03; N, 11.66. Found: C, 69.62; H, 5.13; N, 11.26.

The following Examples 48–87 were prepared by synthetic procedures analogous to the procedures used to synthesize Examples 1–47.

EXAMPLE 48

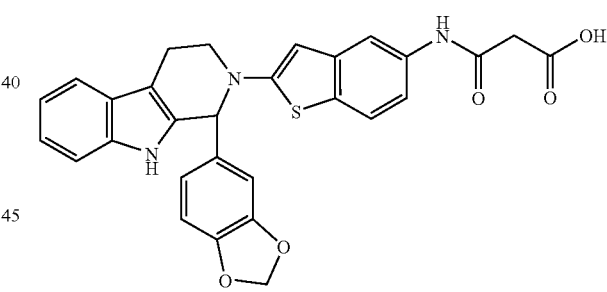

EXAMPLE 49

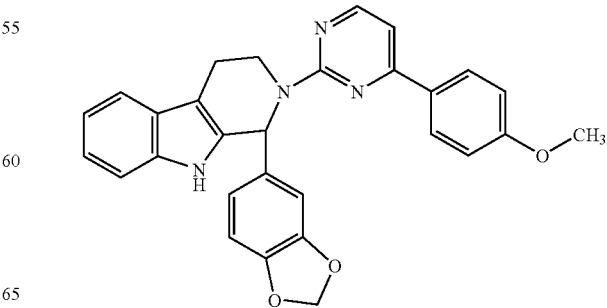

EXAMPLE 50
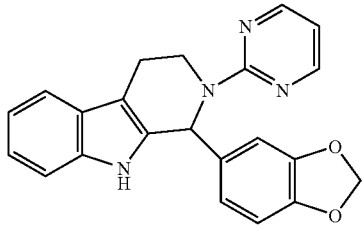
EXAMPLE 51
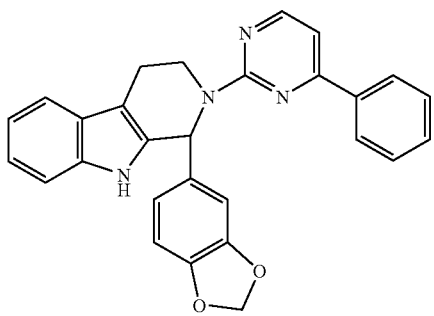
EXAMPLE 52
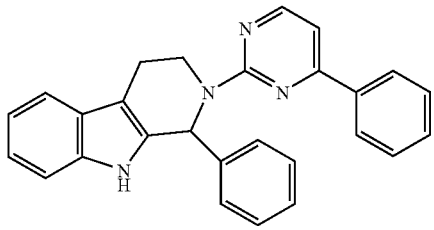
EXAMPLE 53
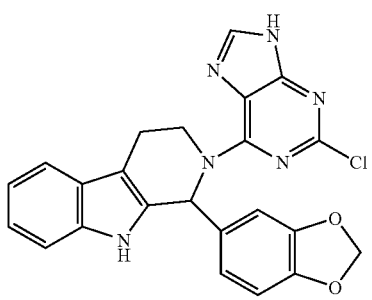
EXAMPLE 54
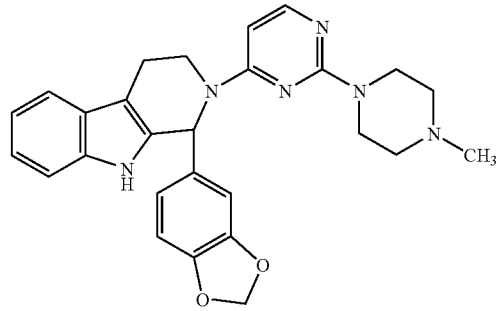
EXAMPLE 55
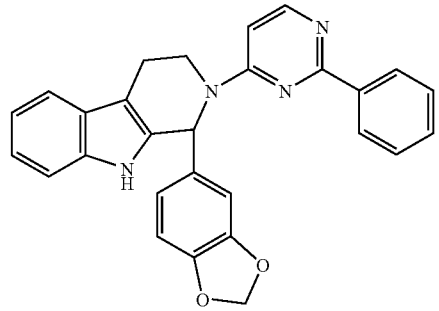
EXAMPLE 56
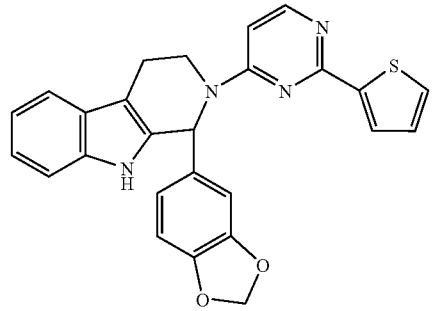
EXAMPLE 57
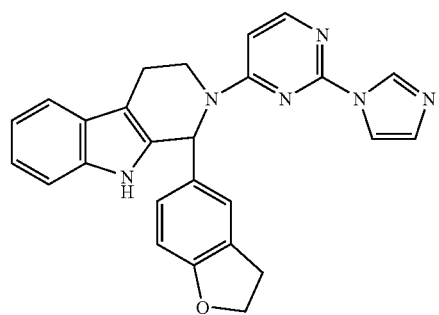

EXAMPLE 58
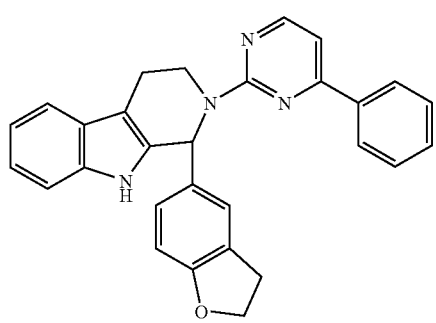
EXAMPLE 61
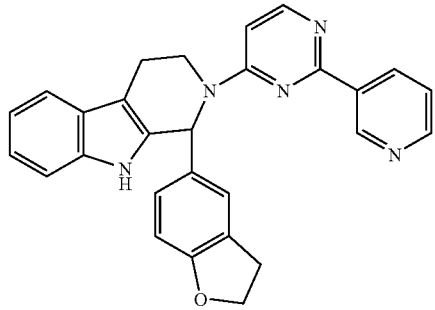
EXAMPLE 59
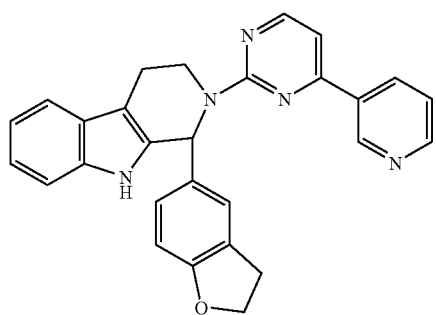
EXAMPLE 62
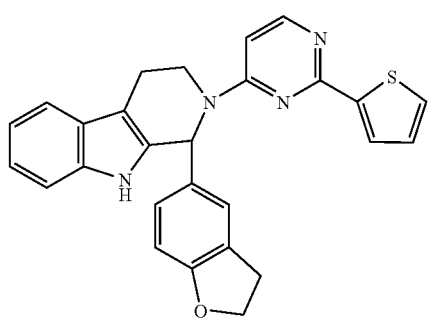
EXAMPLE 60
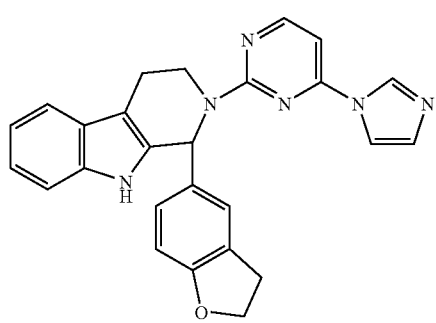
EXAMPLE 63
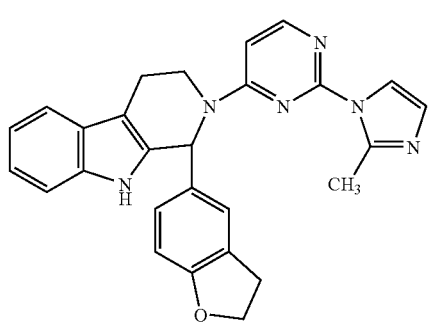

EXAMPLE 64
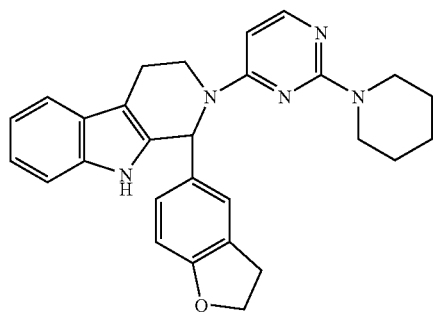
EXAMPLE 67
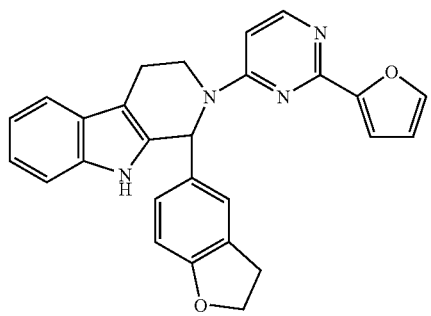
EXAMPLE 65
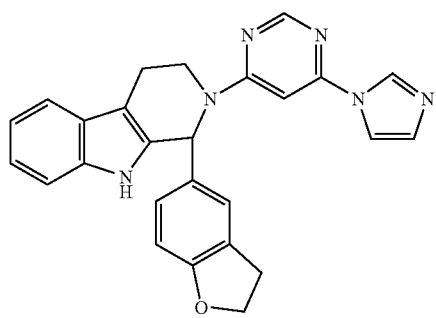
EXAMPLE 68
EXAMPLE 66
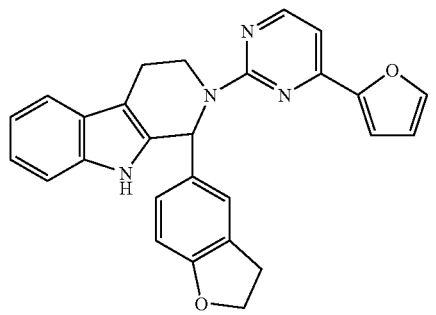
EXAMPLE 69
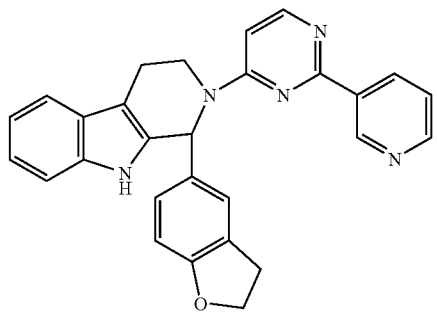

EXAMPLE 70
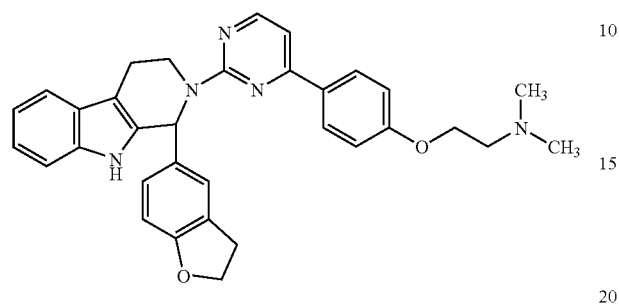
EXAMPLE 71
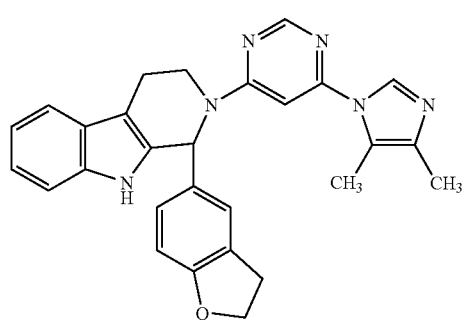
EXAMPLE 72
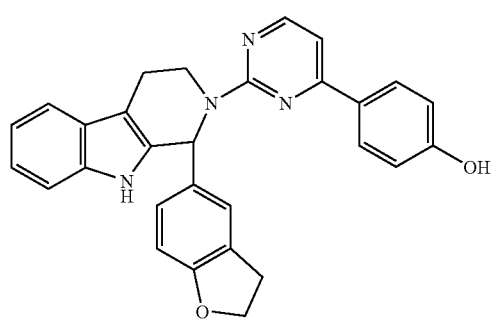
EXAMPLE 73
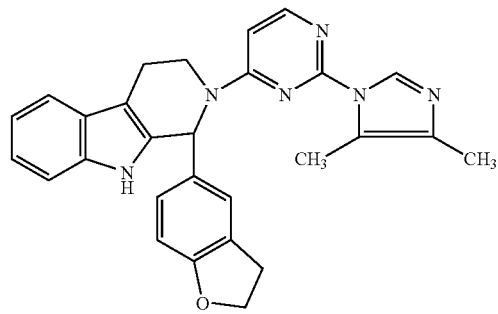
EXAMPLE 74
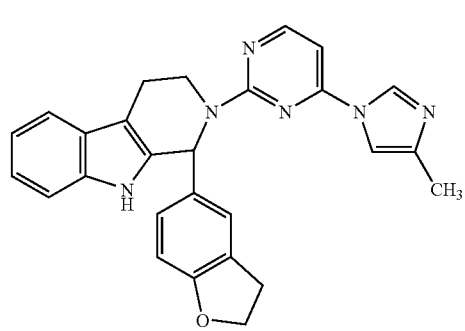
EXAMPLE 75
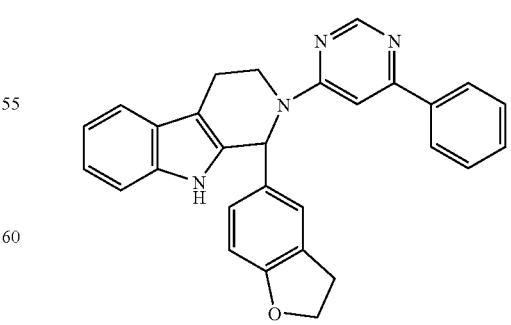

EXAMPLE 76
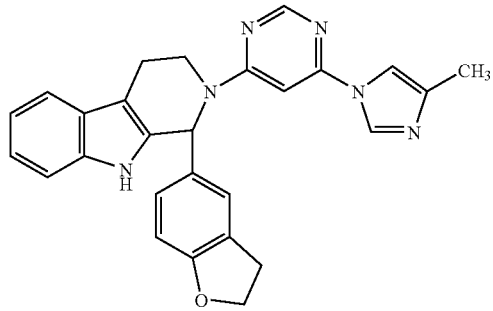
EXAMPLE 77
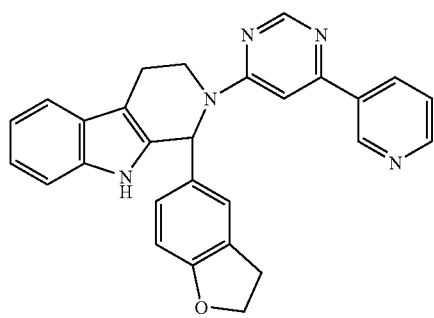
EXAMPLE 78
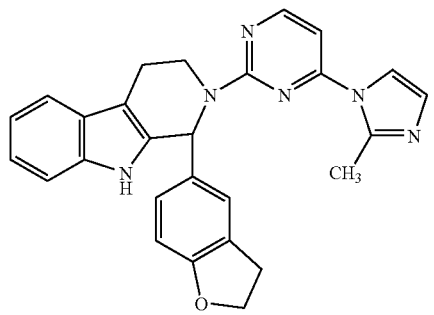
EXAMPLE 79
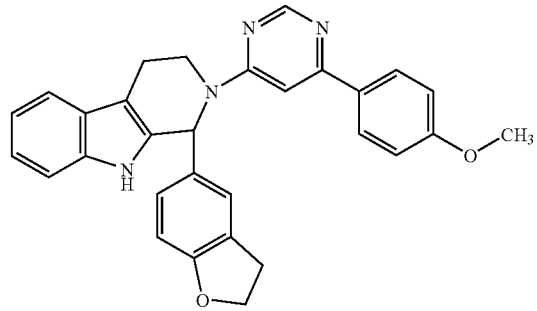
EXAMPLE 80
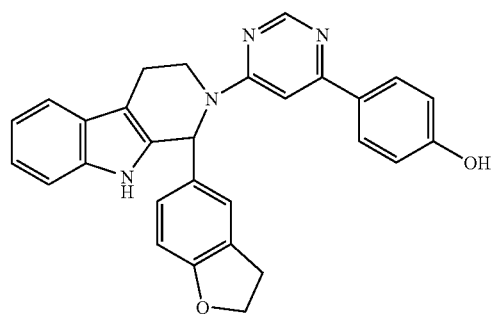
EXAMPLE 81
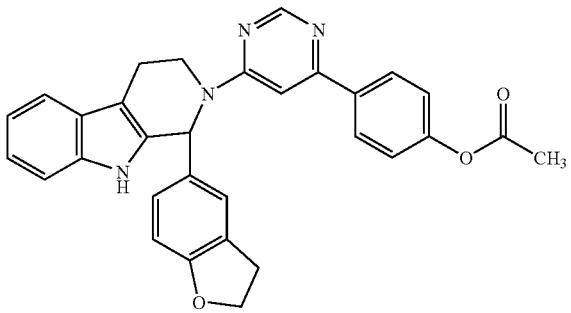

EXAMPLE 82

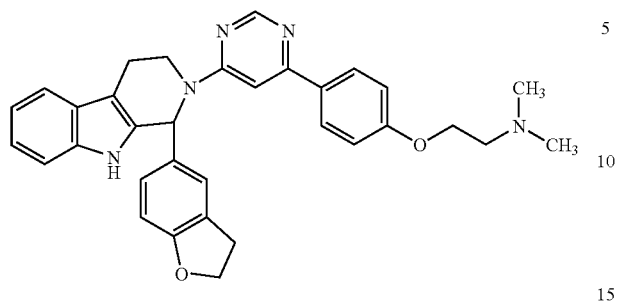

EXAMPLE 86

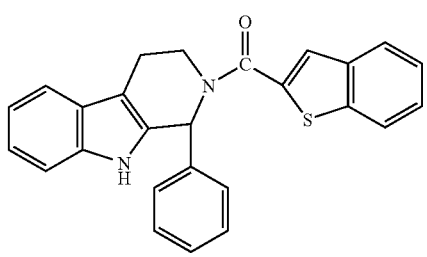

EXAMPLE 83

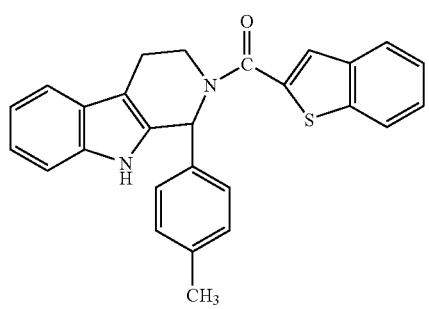

EXAMPLE 87

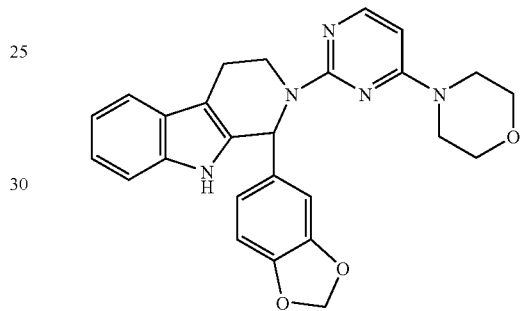

EXAMPLE 84

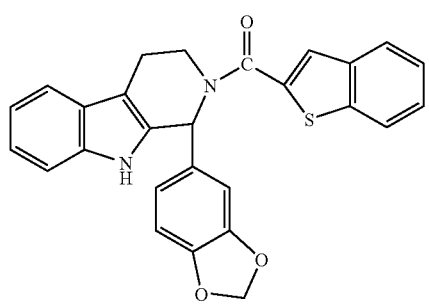

EXAMPLE 85

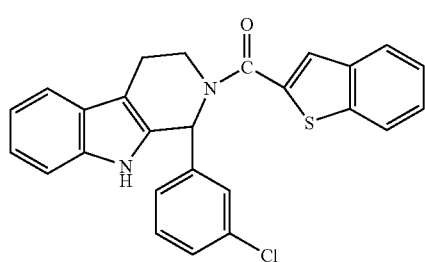

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds pounds of structural formula (I) were determined using recombinant human PDE5.

The compounds of the present invention typically exhibit an $IC_{50}$ value against recombinant human PDE5 of less than about 50 µM, and preferably less than about 25 µM, and more preferably less than about 15 µm. The compounds of the present invention typically exhibit an $IC_{50}$ value against recombinant human PDE5 of less than about 1 µM, and often less than about 0.05 µM. To achieve the full advantage of the present invention, a present PDE5 inhibitor has an $IC_{50}$ of about 0.1 nM to about 15 µM.

The production of recombinant human PDEs and the IC50 determinations can be accomplished by well-known methods in the art. Exemplary methods are described as follows:

EXPRESSION OF HUMAN PDES

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

HUMAN PHOSPHODIESTERASE PREARATIONS

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or ([32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 µL reaction mixture containing (final concentratrations) 40 mM Tris HCl (pH 8.0), 1 µM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) µg of Crotalus atrox venom then was added, and the incubation was continued for 3 minutes (15 minutes total). The reaction was stopped by addition of 200 µL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 µM $ZnSO_4$). Cells were lysed in a Microfluidizer® (Microfluidics Corp.) using nitrogen at 20,000 psi. The lysate was centrifuged and filtered through 0.45 µm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM $MgCl_2$, 0.25 mM DTT, 10 µM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 µM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 µM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 µmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 µg/ml 5'-Nucleotidase, 1 mM EGTA, and 0.15 µM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 µM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM (i.e., 0.5 µM). In vitro test data for representative compounds of the invention is given in the following table:

TABLE 1

| Example | PDE5 $IC_{50}$ (µM) |
|---|---|
| 1 | 0.566 |
| 2 | 0.71 |
| 3 | 0.44[1] |
| 4 | 0.05[1] |
| 5 | 0.2 |
| 6 | 0.67 |
| 7 | 0.55 |
| 8 | 0.19 |
| 9 | 0.44 |
| 10 | 0.76 |
| 11 | 0.44 |
| 12 | 0.18[1] |
| 13a | 0.48 |
| 13b | 0.02 |
| 14 | 0.2[1] |
| 15 | 0.001[1] |
| 16 | 0.07[1] |
| 17 | 0.25[1] |
| 18 | 0.11 |
| 19 | 0.25 |
| 20 | 0.42 |
| 21 | 0.13 |
| 22 | 0.08 |
| 23 | 0.36 |
| 24 | 0.03 |
| 25 | 0.04 |
| 26 | 0.9 |
| 27 | 0.04 |
| 28 | 0.12 |

TABLE 1-continued

| Example | In vitro Results PDE5 IC$_{50}$ (μM) |
|---|---|
| 29 | 0.3 |
| 30 | 0.06 |
| 31 | 0.04 |
| 32 | 0.48 |
| 33 | 0.2 |
| 34 | 0.46 |
| 35 | 0.41 |
| 36 | 0.11 |
| 37 | 0.04 |
| 38 | 0.03 |
| 39 | 0.4 |
| 40 | 0.32 |
| 41 | 0.24 |
| 42 | 0.85 |
| 43 | 0.29 |
| 44 | 0.49 |
| 45 | 0.22 |
| 46 | 0.005 |
| 47a | 0.027 |
| 47b | 0.005 |
| 48 | 0.02 |
| 49 | 0.01 |
| 50 | 0.78 |
| 51 | 0.03 |
| 52 | 0.29 |
| 53 | 0.07 |
| 54 | 0.56 |
| 55 | 0.02 |
| 56 | 0.04 |
| 57 | 0.06 |
| 58 | 0.03 |
| 49 | 0.04 |
| 60 | 0.07 |
| 61 | 0.04 |
| 62 | 0.05 |
| 63 | 0.04 |
| 64 | 0.76 |
| 65 | 0.02 |
| 66 | 0.34 |
| 67 | 0.07 |
| 68 | 0.02 |
| 69 | 0.009 |
| 70 | 0.02 |
| 71 | 0.02 |
| 72 | 0.01 |
| 73 | 0.03 |
| 74 | 0.04 |
| 75 | 0.007 |
| 76 | 0.01 |
| 77 | 0.004 |
| 78 | 0.06 |
| 79 | 0.004 |
| 80 | 0.05 |
| 81 | 0.003 |
| 82 | 0.005 |
| 83 | 0.082 |
| 84 | 0.309 |
| 85 | 0.835 |
| 86 | 0.90 |
| 87 | 1.01 |

[1]versus bovine aorta.

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

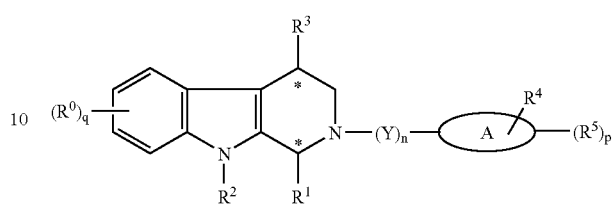

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, $C(=O)R^a$, $OC(=O)R^a$, $C(=O)OR^a$, $C_{1-4}$alkyleneNR$^a$R$^b$, $C_{1-4}$alkyleneHet, $C_{1-4}$alkyleneC(=O)OR$^a$, $C(=O)NR^aSO_2R^c$, $C(=O)C_{1-4}$alkyleneHet, $C(=O)NR^aR^b$, $C(=O)NR^bR^c$, $C(=O)$-NR$^a$C$_{1-4}$alkyleneOR$^b$, $C(=O)NR^aC_{1-4}$alkyleneHet, $OR^a$, $OC_{1-4}$alkyleneC(=O)OR$^a$, $OC_{1-4}$alkyleneNR$^a$R$^b$, $OC_{1-4}$alkyleneHet, $OC_{1-4}$alkyleneOR$^a$, $OC_{1-4}$alkyleneNR$^a$C(=O)OR$^b$, $NR^aR^b$, $NR^bR^c$, $NR^aC_{1-4}$alkyleneNR$^a$R$^b$, $NR^aC(=O)R^b$, $NR^aC(=O)NR^aR^b$, $N(SO_2C_{1-4}$alkyl)$_2$, $NR^a(SO_2C_{1-4}$alkyl), nitro, trifluoromethyl, trifluoromethoxy, cyano, $SO_2NR^aR^b$, $SO_2R^a$, $SOR^a$, $SR^a$, and $OSO_2CF_3$;

$R^1$ is selected from the group consisting of optionally substituted aryl, optionally substituted heteroaryl, an optionally substituted $C_{3-8}$cycloalkyl ring, an optionally substituted $C_{3-8}$heterocycloalkyl ring, an optionally substituted bicyclic ring

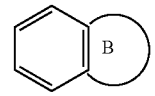

wherein the fused ring B is a 5- or 6-membered ring, saturated or partially or fully unsaturated, and contains carbon atoms and optionally one to three heteroatoms selected from oxygen, sulfur, and nitrogen, hydrogen, arylC$_{1-3}$alkyl, haloC$_{1F-6}$alkyl, C$_{1-4}$alkyleneC(=O)OR$^a$, C$_{1-4}$alkyleneC(=O)NR$^a$R$^b$, C$_{3-8}$cycloalkyl, C$_{3-8}$cycloalkenyl, C$_{3-8}$heterocycloalkenyl, C$_{1-4}$alkyleneHet, C$_{1-4}$alkyleneQR$^a$, C$_{2-6}$alkenyleneQR$^a$, C$_{1-4}$alkyleneQC$_{1-4}$alkyleneQR$^a$,

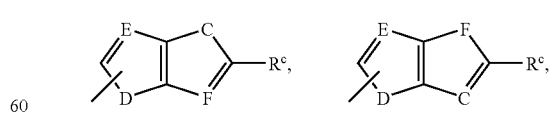

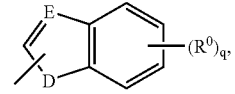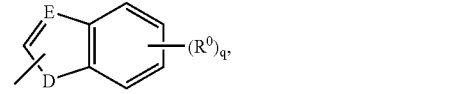

and a spiro substituent having a structure

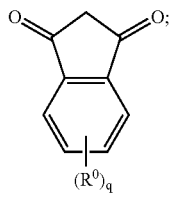

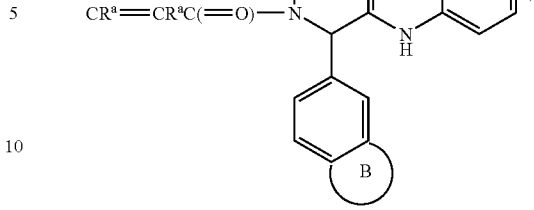

R² is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, aryl$C_{1-3}$alkyl, aryl, heteroaryl, $C(=O)R^a$, $C(=O)NR^aR^b$, $C(=O)NR^bR^c$, $C(=S)NR^aR^b$, $C(=S)NR^bR^c$, $OR^a$, $NR^aR^b$, $NR^bR^c$, $SO_2R^a$, $SO_2NR^aR^b$, $S(=O)R^a$, $S(=O)NR^aR^b$, $C(=O)NR^aC_{1-4}$alkylene$OR^a$, $C(=O)NR^cC_{1-4}$alkylene-Het, $C(=O)C_{1-4}$alkylenearyl, $C(=O)C_{1-4}$alkyleneheteroaryl, $C_{1-4}$alkylenearyl, $C_{1-4}$alkyleneheteroaryl, $C_{1-4}$alkyleneHet, $C_{1-4}$alkyleneC$(=O)C_{1-4}$alkylenearyl, $C_{1-4}$alkyleneC$(=O)C_{1-4}$alkyleneheteroaryl, $C_{1-4}$alkyleneC$(=O)$Het, $C_{1-4}$alkyleneC$(=O)NR^bR^c$, $C_{1-4}$alkyleneOR$^a$, $C_{1-4}$alkyleneNR$^a$C$(=O)R^a$, $C_{1-4}$alkyleneOC$_{1-4}$alkyleneOR$^a$, $C_{1-4}$alkyleneNR$^b$R$^c$, $C_{1-4}$alkyleneC$(=O)OR^a$, and $C_{1-4}$alkyleneOC$_{1-4}$alkyleneC$(=O)OR^a$;

R³ is selected from the group consisting of hydrogen, $C_{1-6}$alkyl, halo$C_{1-6}$alkyl, aryl, heteroaryl, aryl$C_{1-3}$alkyl, heteroaryl$C_{1-3}$alkyl, $C_{1-3}$alkylenearyl, $C_{1-3}$alkyleneHet, $C_{3-8}$cycloalkyl, and $C_{3-8}$heterocycloalkyl;

Y is selected from the group consisting of $C(=O)Z$, SO, $C(=S)$, and $CR^a=CR^a$;

Z is $(CH_2)_t$ or $C\equiv C$;

A is selected from the group consisting of furanyl, thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, 1,2,4-oxadiazolyl, 1,2,5-oxadiazolyl, 1,3,4-oxadiazolyl, 1,2,3,4-oxatriazolyl, 1,2,3,5-oxatriazolyl, pyridinyl, pyridazinyl, pyrimidinyl, pyrazinyl, 1,3,5-triazinyl, 1,2,4-triazinyl, 1,2,3-triazinyl, indolizinyl, indolyl, isoindolyl, benzo[b]furanyl, benzo[b]thienyl, 1H-indazolyl, benzimidazolyl, benzthiazoyl, purinyl, 4H-quinolizinyl, quinolinyl, isoquinolinyl, and naphthyl;

R⁴ is selected from the group consisting of hydrogen, $C_{1-6}$alkyl, aryl, heteroaryl, halo, $C(=O)OR^b$, $NHC(=O)C_{1-3}$alkyleneN$(R^b)_2$, $NO_2$, $C(=O)OR^b$, $OR^b$, $CF_3$, $OR^a$, CN, $OC(=O)R^b$, aryl$OR^b$, Het, $NR^aC(=O)C_{1-3}$alkyleneC$(=O)OR^a$, aryl$OC_{1-3}$alkyleneNR$^a$R$^b$, aryl$OC(=O)R^a$, $C_{1-4}$alkyleneC$(=O)OR^b$, $OC_{1-4}$alkyleneC$(=O)OR^b$, $C_{1-4}$alkyleneOC$_{1-4}$alkyleneC$(=O)OR^b$, $C(=O)NR^bSO_2R^c$, $C_{1-4}$alkyleneNR$^b$R$^c$, $C_{2-6}$alkenyleneNR$^b$R$^c$, $C(=O)NR^cC_{1-4}$alkyleneOR$^b$, $C(=O)NR^cC_{1-4}$alkyleneHet, $OC_{2-4}$alkyleneNR$^b$R$^c$, $OC_{1-4}$alkyleneCH(OR$^b$)CH$_2$NR$^b$R$^c$, $OC_{1-4}$alkyleneHet, $OC_{2-4}$alkyleneOR$^b$, $OC_{2-4}$alkyleneNR$^b$C$(=O)OR^c$, $NR^bC_{1-4}$alkyleneNR$^b$R$^c$, $NR^bC(=O)R^c$, $NR^bC(=O)NR^bR^c$, $N(SO_2C_{1-4}$alkyl$)_2$, $NR^b(SO_2C_{1-4}$alkyl$)$, $SO_2NR^bR^c$, $OSO_2CF_3$, $C(=O)R^b$, $C_{1-3}$alkylenearyl, $C_{1-4}$alkyleneHet, $C_{1-6}$alkyleneOR$^b$, $C_{1-3}$alkyleneN$(R^b)_2$, $NR^bR^c$, $C(=O)NR^bR^c$, $NHC(=O)C_{1-3}$alkylenearyl, $NHC(=O)C_{1-3}$alkyleneheteroaryl, $C_{3-8}$cycloalkyl, $C_{3-8}$heterocycloalkyl, aryl$OC_{1-3}$alkyleneN$(R^b)_2$, aryl$OC(=O)R^b$, $NRC(=O)C_{1-3}$alkyleneC$_{3-8}$heterocycloalkyl, $NHC(=O)C_{1-3}$alkyleneHet, $NHC(=O)$halo$C_{1-6}$alkyl, and R⁵, independently, is selected from the group consisting of halo, $NR^aR^b$, $NO_2$, $C_{1-6}$alkyl, oxo, and $OR^a$;

or R⁴ and R⁵ are taken together to form a 3- or 4-membered alkylene or alkenylene chain component of a 5- or 6-membered ring, optionally containing at least one heteroatom;

R$^a$ is selected from the group consisting of hydrogen, $C_{1-6}$alkyl, cyano, aryl, aryl$C_{1-3}$alkyl, $C_{1-3}$alkylenearyl, heteroaryl, heteroaryl$C_{1-3}$alkyl, and $C_{1-3}$alkyleneheteroaryl;

R$^b$ is selected from the group consisting of hydrogen, $C_{1-6}$alkyl, $C_{3-8}$cycloalkyl, $C_{1-3}$alkyleneN$(R^a)_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

R$^c$ is selected from the group consisting of hydrogen, $C_{1-6}$alkyl, aryl, heteroaryl, aryl$C_{1-3}$alkyl, heteroaryl$C_{1-3}$alkyl, $C_{1-3}$alkyleneN$(R^a)_2$, $C_{1-6}$alkylenearyl, $C_{1-6}$alkyleneHet, halo$C_{1-6}$alkyl, $C_{3-8}$cycloalkyl, $C_{3-8}$heterocycloalkyl, Het, $C_{1-3}$alkyleneheteroaryl, $C_{1-6}$alkyleneC$(=O)OR^a$, and $C_{1-3}$alkyleneC$_{3-8}$heterocycloalkyl;

or R$^b$ and R$^c$ are taken together to form a 5- or 6-membered ring, optionally containing at least one heteroatom;

Q is O, S, or $NR^d$;

C is O, S, or $NR^d$;

D is O, S, or $NR^a$;

E is $CR^a$ or N;

F is $CR^a$, $C(R^a)_2$, or $NR^d$;

R$^d$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or $C(=O)OR^a$;

n is 1;

p is 0, 1, 2, or 3;

q is 0, 1, 2, 3, or 4;

t is 1, 2, 3, or 4;

or a pharmaceutically acceptable salt or solvate thereof.

2. The compound of claim 1 represented by the formula

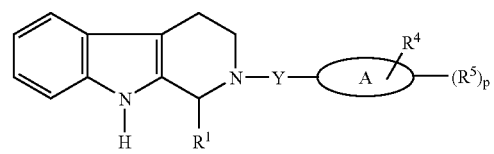

wherein $R^1$ is selected from the group consisting of optionally substituted aryl, optionally substituted heteroaryl, an optionally substituted bicyclic ring

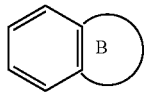

wherein the fused ring B is a 5- or 6-membered ring, saturated or partially or fully unsaturated, and contains carbon atoms and optionally one to three heteroatoms selected from oxygen, sulfur, and nitrogen;

Y is selected from the group consisting of $C(=O)C\equiv C$, $C(=O)(CH_2)_t$, and $C(=S)$;

$R^4$ is selected from the group consisting of hydrogen, aryl, heteroaryl, halo, $C(=O)OR^b$, $NHC(=O)C_{1-3}$alkyleneN$(R^b)_2$, $NO_2$, $C(=O)OR^b$, $OR^b$, $CF_3$, $OR^a$, $CN$, $OC(=O)R^b$, arylOR$^b$, Het, $NR^aC(=O)C_{1-3}$alkyleneC$(=O)OR^a$, arylOC$_{1-3}$alkyleneNR$^aR^b$, arylOC$(=O)R^a$, $C_{1-4}$alkyleneC$(=O)OR^b$, $OC_{1-4}$alkyleneC$(=O)OR^b$, $C(=O)NR^bSO_2R^c$, $C_{1-4}$alkyleneNR$^bR^c$, $C_{2-6}$alkenyleneNR$^bR^c$, $C(=O)NR^bC_{1-4}$alkyleneOR$^b$, $NR^bC_{1-4}$alkyleneNR$^bR^c$, $NR^bC(=O)R^c$, $NR^bC(=O)NR^bR^c$, $OSO_2CF_3$, $C(=O)R^b$, $C_{1-4}$alkyleneHet, $C_{1-6}$alkyleneOR$^b$, $C_{1-3}$alkyleneN$(R^b)_2$, $NR^bR^c$, $C(=O)NR^bR^c$, $NHC(=O)C_{1-3}$alkylenearyl, $NHC(=O)C_{1-3}$alkyleneheteroaryl, $NHC(=O)C_{1-3}$alkyleneHet, $NHC(=O)$haloC$_{1-6}$alkyl, and

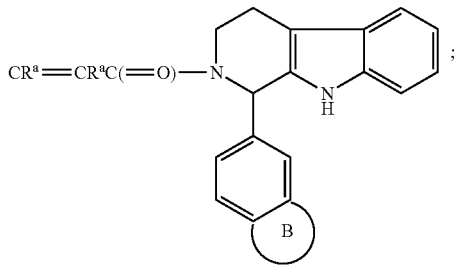

$R^5$, independently, is selected from the group consisting of halo, $NR^aR^b$, $NO_2$, $C_{1-6}$alkyl, oxo, and $OR^a$;

$R^a$ and $R^b$, independently, are selected from the group consisting of hydrogen, $C_{1-6}$alkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^c$ is selected from the group consisting of hydrogen, $C_{1-6}$alkyl, aryl, heteroaryl, aryl$C_{1-3}$alkyl, heteroaryl$C_{1-3}$alkyl, $C_{1-3}$alkyleneN$(R^a)_2$, $C_{1-6}$alkylenearyl, $C_{1-6}$alkyleneHet, haloC$_{1-6}$alkyl, $C_{3-8}$cycloalkyl, $C_{3-8}$heterocycloalkyl, Het, $C_{1-3}$alkyleneheteroaryl, $C_{1-6}$alkyleneC$(=O)OR^a$, and $C_{1-3}$alkyleneC$_{3-8}$heterocycloalkyl;

or $R^b$ and $R^c$ are taken together to form a 5- or 6-membered ring, optionally containing at least one heteroatom;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or $C(=O)OR^a$;

p is 0, 1, 2, or 3;

t is 1, 2, 3, or 4;

or a pharmaceutically acceptable salt or solvate thereof.

3. The compound of claim 1 represented by the formula

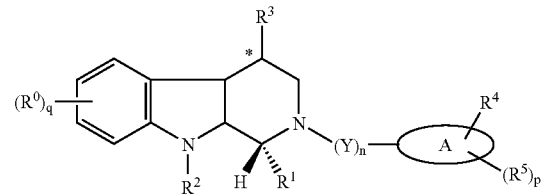

or a pharmaceutically acceptable salt or hydrate thereof.

4. The compound of claim 1 wherein q is 0.

5. The compound of claim 1 wherein $R^0$ is selected from the group consisting of $C_{1-6}$alkyl, aryl, heteroaryl, $C_{3-8}$heterocycloalkyl, $OR^a$, $C(=O)OR^a$, $C_{1-4}$alkyleneNR$^aR^b$, $OC(=O)R^a$, $C(=O)R^a$, $NR^bR^c$, $C_{3-8}$cycloalkyl, $C_{3-8}$cycloalkylQ, $C(=O)NR^aR^b$, and $C(=O)NR^bR^c$.

6. The compound of claim 1 wherein $R^1$ is selected from the group consisting of $C_{1-4}$alkyleneQR$^a$, $C_{1-4}$alkyleneQC$_{1-4}$alkyleneQR$^a$, $C_{3-8}$cycloalkyl, $C_{3-8}$cycloalkenyl, $C_{1-6}$alkyl,

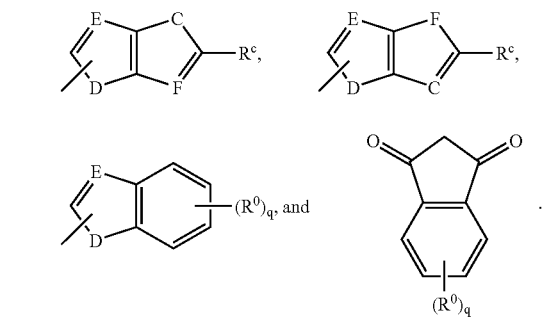

7. The compound of claim 1 wherein $R^1$ is the optionally substituted bicyclic ring

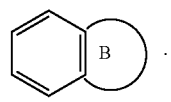

8. The compound of claim 7 wherein $R^1$ is

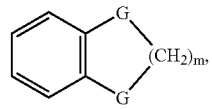

and wherein m is an integer 1 or 2, and G, independently, are $C(R^a)_2$, O, S, or $NR^a$.

9. The compound of claim 1 wherein $R^1$ is selected from the group consisting of

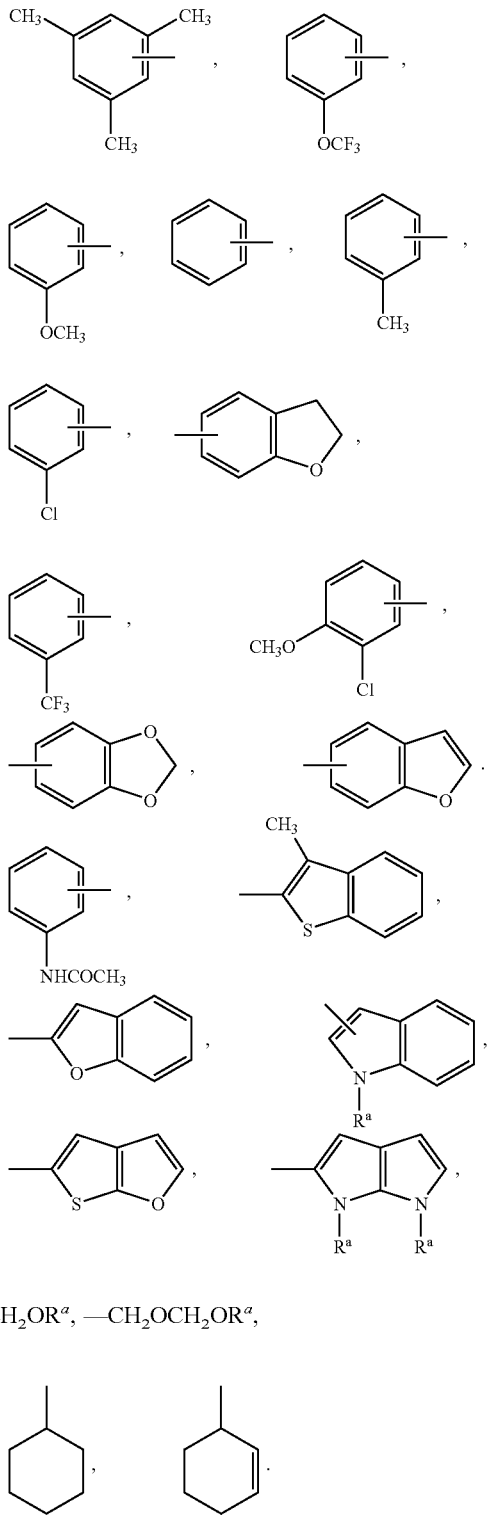

—CH$_2$OR$^a$, —CH$_2$OCH$_2$OR$^a$,

10. The compound of claim 1 wherein the $R^2$ group is selected from the group consisting of hydrogen, aryl, heteroaryl, OR$^a$, NR$^a$R$^b$, NR$^b$R$^c$, C$_{1-4}$alkyleneHet, C$_{1-4}$alkyleneheteroaryl, C$_{1-4}$alkylenearyl, C$_{1-4}$alkyleneC(=O)C$_{1-4}$alkylenearyl, C$_{1-4}$alkyleneC(=O)OR$^a$, C$_{1-4}$alkyleneC(=O)NR$^b$R$^c$, C$_{1-4}$alkyleneC(=O)Het, C$_{1-4}$alkyleneNR$^b$R$^c$, C$_{1-4}$alkyleneNR$^a$C(=O)R$^a$, and C$_{1-4}$alkyleneOC$_{1-4}$-alkyleneOR$^a$.

11. The compound of claim 1 wherein $R^4$ is selected from the group consisting of hydrogen, C$_{1-6}$alkyl, aryl, heteroaryl, halo, C(=O)OR$^b$, NHC(=O)C$_{1-3}$alkyleneN(R$^b$)$_2$, NO$_2$, C(=O)OR$^b$, OR$^b$, CF$_3$, OR$^a$, CN, OC(=O)R$^b$, arylOR$^b$, Het, NR(=O)C$_{1-3}$alkyleneC(=O)OR$^a$, arylOC$_{1-3}$alkyleneNR$^a$R$^b$, arylOC(=O)R$^a$, C$_{1-4}$alkyleneC(=O)OR$^b$, OC$_{1-4}$alkyleneC(=O)OR$^b$, C(=O)NR$^b$SO$_2$R$^c$, C$_{1-4}$alkyleneNR$^b$R$^c$, C$_{2-6}$alkenyleneNR$^b$R$^c$, C(=O)NR$^b$C$_{1-4}$alkyleneOR$^b$, NR$^b$C$_{1-4}$alkyleneNR$^b$R$^c$, NR$^b$C(=O)R$^c$, NR$^b$C(=O)NR$^b$R$^c$, OSO$_2$CF$_3$, C(=O)R$^b$, C$_{1-3}$alkylenearyl, C$_{1-4}$alkyleneHet, C$_{1-6}$alkyleneOR$^b$, C$_{1-3}$alkyleneN(R$^b$)$_2$, NR$^b$R$^c$, C(=O)NR$^b$R$^c$, NHC(=O)C$_1$–C$_3$alkylenearyl, C$_{3-8}$cycloalkyl, C$_{3-8}$heterocycloalkyl, NHC(=O)C$_{1-3}$alkyleneHet, NHC(=O)haloC$_{1-6}$alkyl, and

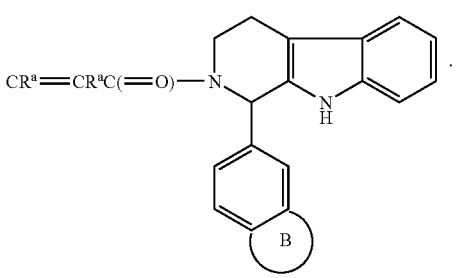

12. The compound of claim 1 wherein $R^3$ is selected from the group consisting of hydrogen, C$_{1-6}$alkyl, aryl, and heteroaryl.

13. The compound of claim 1 wherein q is 0 or $R^0$ is selected from the group consisting of halo, methyl, trifluoromethyl, and trifluoromethoxy; $R^1$ is selected from the group consisting of

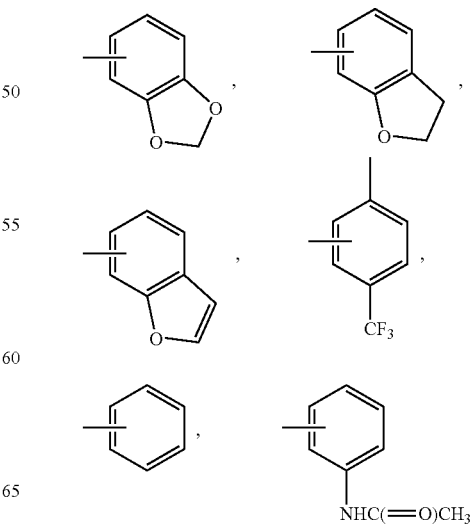

-continued

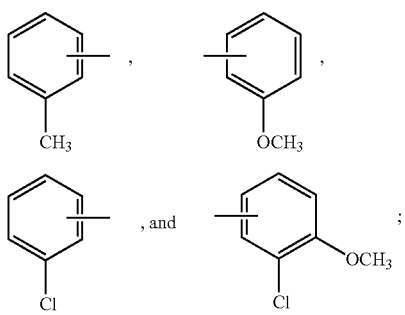

$R^2$ is selected from the group consisting of hydrogen, $C_{1-6}$alkyl, $C(=O)NR^bR^c$, and $C_{1-4}$alkyleneHet; $R^3$ is selected from the group consisting of hydrogen, $C_{1-6}$alkyl, aryl, and heteroaryl; Y is selected from the group consisting of $C(=O)C\equiv C$, $C(=O)CH_2$, and $C(=O)CH_2CH_2$; A is

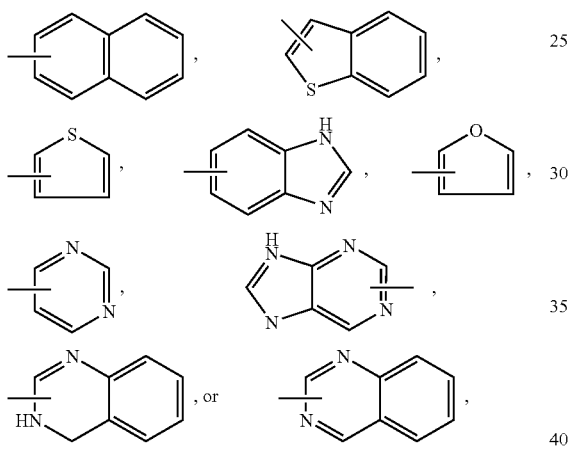

$R^4$ is selected from the group consisting of H, $NHC(=O)CH_3$, $N(CH_3)_2$, $C(=O)NH_2$, $NHCH_3$, $NO_2$, $NH_2$, Br, $C(=O)CH_3$, $OCH_3$, $CH_2OCH_3$, $NHC(=O)CH_2N(CH_3)_2$, $CH_2N(CH_3)_2$, $CH_3$, Cl, $NHC(=O)CH_2CO_2H$,

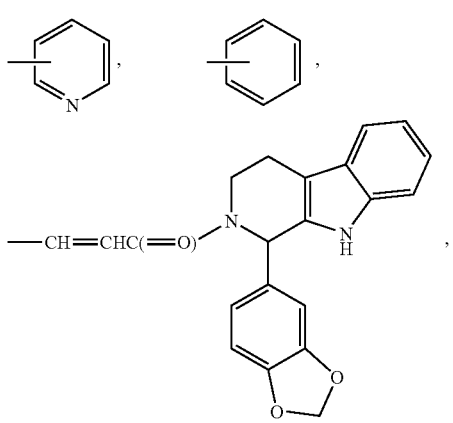

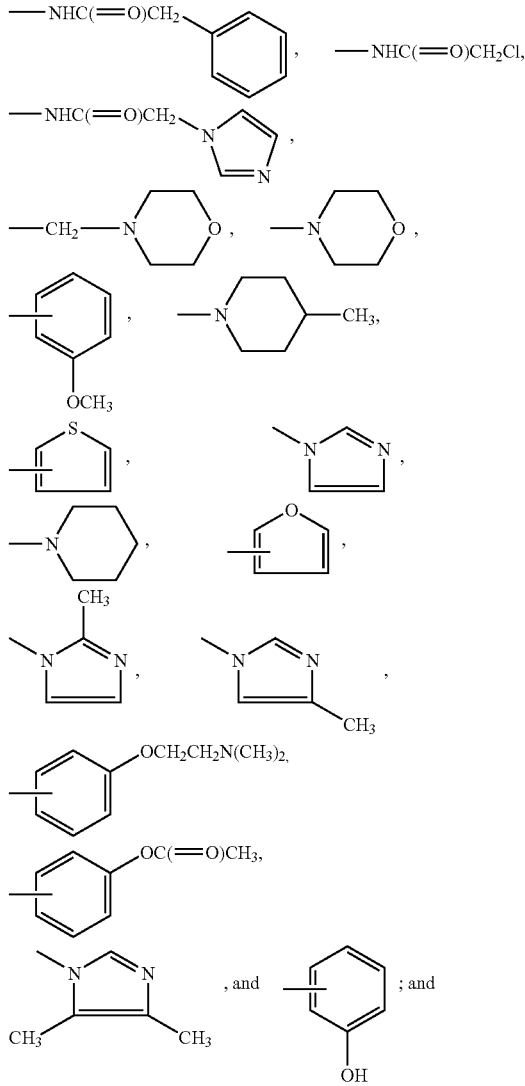

p is 0 or R groups, independently, are selected from the group consisting of $CH_3$, Cl, oxo, and $OCH_3$.

14. The compound of claim 13 wherein $R^2$ is hydrogen and $R^3$ is hydrogen.

15. A compound 1-(1-benzo[1,3]dioxol-5-yl-1,3,4,9-tetrahydro-β-carbolin-2-yl)-1-(3H-benzoimidazol-5-yl)methanone; 2-benzo[b]thiophen-3-yl-1-(1-benzo[1,3]dioxol-5-yl-1,3,4,9-tetrahydro-β-carbolin-2-yl)ethanone;

or a pharmaceutically acceptable salt or solvate thereof.

16. A pharmaceutical composition comprising a compound of claim 1, together with a pharmaceutically acceptable diluent or carrier.

17. A method for the curative or prophylactic treatment of male erectile dysfunction, comprising administration of an effective dose of a compound of claim 1, or a pharmaceutically acceptable salt or solvate thereof, to an animal.

18. The method of claim 17 wherein the treatment is an oral treatment.

* * * * *

UNITED STATES PATENT AND TRADEMARK OFFICE
CERTIFICATE OF CORRECTION

PATENT NO.       : 7,022,856 B2                                   Page 1 of 3
APPLICATION NO.  : 10/470407
DATED            : April 4, 2006
INVENTOR(S)      : Orme et al.

It is certified that error appears in the above-identified patent and that said Letters Patent is hereby corrected as shown below:

On Title Page

Page 1, item (73), "LIlly Icos LLC" should be -- Lilly ICOS LLC --

Column 5, line 50, delete the comma after "haloalkyl"

Column 13, line 23, delete "selected from the group consisting of"

Column 21, line 62, delete the comma before "from,"

Column 25, line 35, "-phenylmethane" should be -- -phenylmethanone --

Column 29, structure shown in Example 12,

" 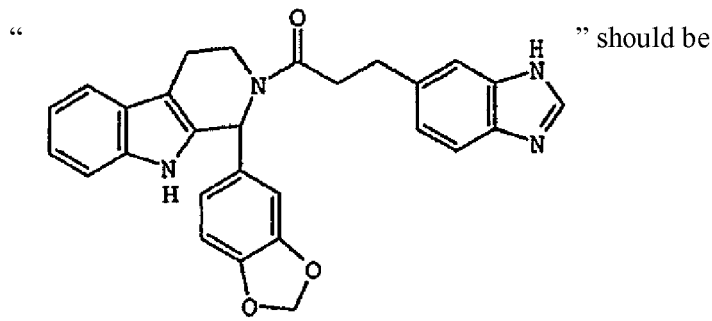 " should be

-- 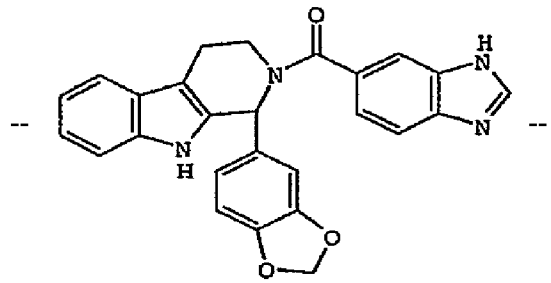 --

UNITED STATES PATENT AND TRADEMARK OFFICE
CERTIFICATE OF CORRECTION

PATENT NO. : 7,022,856 B2
APPLICATION NO. : 10/470407
DATED : April 4, 2006
INVENTOR(S) : Orme et al.

It is certified that error appears in the above-identified patent and that said Letters Patent is hereby corrected as shown below:

Column 30, line 18, "Example 1-12" should be -- Examples 1-12 --

Column 13, structure shown in Example 13a,

" 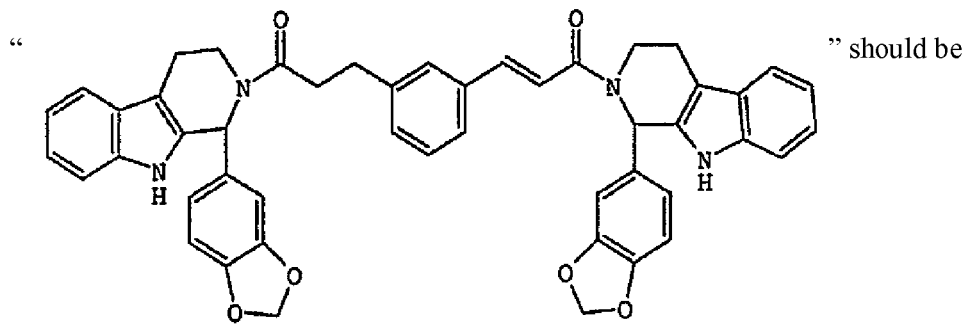 " should be

-- 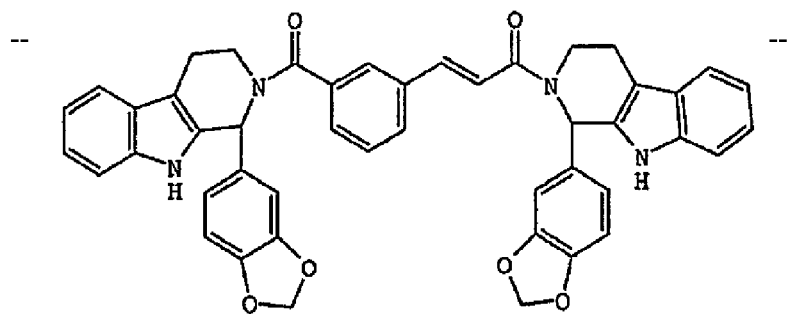 --

Column 54, line 51, delete "pounds"

Column 54, line 63, "IC50" should be -- $IC_{50}$ --

Column 55, line 1, "PDES" should be -- PDEs --

Column 55, line 16, "2xSC-leu" should be -- 2X SC-leu --

Column 55, line 18, "2xYET/" should be -- 2X YET/ --

Column 55, line 23, "PREARATIONS" should be -- PREPARATIONS --

UNITED STATES PATENT AND TRADEMARK OFFICE
CERTIFICATE OF CORRECTION

PATENT NO. : 7,022,856 B2
APPLICATION NO. : 10/470407
DATED : April 4, 2006
INVENTOR(S) : Orme et al.

It is certified that error appears in the above-identified patent and that said Letters Patent is hereby corrected as shown below:

Column 56, line 18, "acetate." should be -- acetate, --

Column 57, line 34, "49" should be -- 59 --

Column 58, line 22, "C(=O) -NR . . ." should be -- C(=O)NR . . . --

Column 58, line 49, "haloC$_{1F-6}$ . . ." should be -- haloC$_{1-6}$ . . . --

Column 59, line 18, ". . . alkylene-Het," should be -- . . . alkyleneHet, --

Column 64, line 11, "NR(=O) . . ." should be -- NR$^a$C(=O) . . . --

Column 65, line 46, ". . . CO2H," should be -- . . . CO$_2$H, --

Column 66, line 45, "R" should be -- R$^5$ --

Signed and Sealed this

Twenty-seventh Day of February, 2007

JON W. DUDAS
*Director of the United States Patent and Trademark Office*